US006858577B1

(12) United States Patent  (10) Patent No.: US 6,858,577 B1
Zhang et al.  (45) Date of Patent: Feb. 22, 2005

(54) INDOLE PEPTIDOMIMETICS AS THROMBIN RECEPTOR ANTAGONISTS

(75) Inventors: Han-Cheng Zhang, Lansdale, PA (US); William J. Hoekstra, Chapel Hill, NC (US); Bruce E. Maryanoff, Forest Grove, PA (US); David F. McComsey, Warminser, PA (US)

(73) Assignees: Ortho-McNeil Pharmaceutical, Inc., Raritan, NJ (US); Millennium Pharmaceuticals, Inc., Cambridge, MA (US)

( * ) Notice: Subject to any disclaimer, the term of this patent is extended or adjusted under 35 U.S.C. 154(b) by 373 days.

(21) Appl. No.: 09/603,231

(22) Filed: Jun. 26, 2000

Related U.S. Application Data

(60) Provisional application No. 60/141,550, filed on Jun. 29, 1999.

(51) Int. Cl.$^7$ .................. A01N 37/18; A61K 38/00; A61K 38/04; A61K 38/06; C07D 277/04

(52) U.S. Cl. .................. 514/2; 514/18; 514/19; 530/330; 530/331; 548/146; 548/215; 548/333.5; 548/335.1

(58) Field of Search .................. 514/2, 19, 18; 530/330, 331; 548/14.6, 215, 333.5, 335.1

(56) References Cited

U.S. PATENT DOCUMENTS

| 4,977,153 A | 12/1990 | Louis et al. ................. 514/237 |
| 5,439,906 A | 8/1995 | Bock et al. .................. 514/220 |
| 5,530,026 A | 6/1996 | Gaudreault et al. ......... 514/524 |
| 6,017,890 A | 1/2000 | Hoekstra et al. |

FOREIGN PATENT DOCUMENTS

| CA | 2011222 A1 | 3/1990 |
| EP | 0 385 850 A2 | 9/1990 |
| WO | WO 92/14750 A1 | 9/1992 |
| WO | WO 93/18026 A1 | 9/1993 |
| WO | WO 99/00357 A1 | 1/1999 |
| WO | WO 99/33798 A1 | 7/1999 |
| WO | WO 99/42475 | 8/1999 |

OTHER PUBLICATIONS

U.S. Appl. No. 09/603,229, McComsey et al.
U.S. Appl. No. 09/599,826, Zhang et al.
U.S. Appl. No. 09/603,338, Zhang et al.
Thrombin Receptor (PAR–1) Antagonists, Heterocycle–Based Peptidomimetics of the SFLLR Agonist Motif, William J. Hoekstra et al., Bioorganic & Medicinal Chem Ltrs 8, pp. 1649–1654, Jul. 7, 1998.
Development of Potent Thrombin Receptor Antagonist Peptides, M.S. Bernatowicz et al., J. Med. Chem vol. 39, pp. 4879–4887, Dec. 6, 1996.
"Heterocycle–Peptide Hybrid Compounds, Aminotriazole–Containing Agonists of the Thrombin Receptor (PAR–1)", David F. McComsey et al., Bioorganic & Medicinal Chemistry Letters 9 (1999), pp. 1423–1428.
"Design, Synthesis, and Structure–Activity Relationship for a Series of Factor XA Inhibitors Containing the Benzimidazoone Nucleus as a Central Template", Charles K. Marlowe et al., Medicinal Chemistry, COR Therapeutics, Inc., Abstract.
"Novel Indole–Based Peptidomimetics as Potent Thrombin Receptor (PAR–1) Antagonists", Han Cheng Zhang et al., The R.W. Johnson Pharmaceutical Research Institute, Abstract.
"Approaches to the Synthesis of Ureapeptoid Peptidomimetics" John A.W. Kruijtzer et al., Tetrahedron Letters, vol. 38, No. 30, pp. 5335–5338, 1997.
"Cloning and Characterization of Human Protease–Activated Receptor 4", Wen–Feng Xu et al., Proc. Natl. Acad. Sci. USA, vol. 95, Jun. 1998, pp. 6642–6646.
"Molecular Cloning of a Proteinase Activated Receptor", Sverker Nystedt et al., Proc. Natl. Acad. Sci. USA, vol. 91, Sep. 1994, pp. 9208–9212.
"Thrombin–Induced Events in Non–Platelet Cells are Mediated by the Unique Proteolytic Mechanism Established for the Cloned Platelet Thrombin Receptor", David T. Hung, et al., The Journal of Cell Biology, vol. 116, No. 3, Feb. 1992, pp. 827–832.
Thrombin Receptor Activation Causes Rapid Neural Cell Rounding and Neurite Retraction Independent of Classic Second Messengers, Kees Jalink et al., The Journal of Cell Biology, vol. 118, No. 2, Jul. 1992, pp. 411–419.
"Thrombin–Induced Expression of Endothelial. P–Selectin and Intercellular Adhesion Molecule–1: A Mechanism for Stabilizing Neutrophil Adhesion", Yasuo Sugama et al., The Journal of Cell Biology, vol. 119, No. 4, Nov. 1992, pp. 935–944.
"*Molecular Cloning of a Functional Thrombin Receptor Reveals a Novel Proteolytic Mechanism of Receptor Activation*", Thien–Khai H. Vu et al., Cell, vol. 64, Mar. 1991, pp. 1057–1068.
"Response of a Human Megakaryocytic Cell Line to Thrombin: Increase in Intracellular Free Calcium and Mitogen Release", Cindy L. A. Jones, et al., Biochemica et Biophysica Acta. 1136, 1992, pp. 272–282.

(List continued on next page.)

*Primary Examiner*—Jezia Riley
(74) *Attorney, Agent, or Firm*—Gabrial Lopez; Hal B. Woodrow

(57) ABSTRACT

The invention is directed to novel indole peptidomimetic compounds which are useful as thrombin receptor antagonists for the treatment of diseases associated with thrombosis, restenosis, hypertension, heart failure, arrhythmia, inflammation, angina, stroke, atherosclerosis, ischemic conditions, Angiogenesis related disorders, cancer, and neurodegenerative disorders. Pharmaceutical compositions comprising the substituted indole peptidomimetics of the present invention and methods of treating conditions mediated by the thrombin receptor are also disclosed.

10 Claims, No Drawings

OTHER PUBLICATIONS

"Thrombin Effects on Osteoblastic Cells—II. Structure–Function Relatoinships" Dimitris N. Tatakis et al., Biochemical and Biophysical Research Communications, vol. 174, No. 1, Jan. 1991, pp. 181–188.

"Condensed Heteroaromatic Ring Systems—XIII. One–Step Synthesis of 2–Substituted 1–Methylsulfoonylindoles From N–(2–Halophenyl) Methanesulfonamides", Takao Sakamoto et al., Chem. Pharm. Bull., No. 4, Sep. 1987, pp. 1305–1308.

"An Antibody Against the Exosite of the Cloned Thrombin Receptor Inhibits Experimental Arterial Thrombosis in the African Green Monkey", Jacquelynn J. Cook et al., *Basic Science Reports*, Oct. 1994, pp. 2961–2971.

"Protease–Activated Receptor 3 is a Second Thrombin Receptor in Human", Hiroaki Ishihara, Nature, vol. 386, Apr. 1997, pp. 502–508.

INDOLE PEPTIDOMIMETICS AS THROMBIN RECEPTOR ANTAGONISTS

This patent application claims priority from provisional patent application Ser. No. 60/141,550, which was filed on Jun. 29, 1999.

FIELD OF THE INVENTION

This invention relates to certain novel thrombin receptor antagonists, their synthesis and their use for the treatment of diseases associated with thrombosis, restenosis, hypertension, heart failure, arrhythmia, inflammation, angina, stroke, atherosclerosis, ischemic conditions, Angiogenesis related disorders, cancer, and neurodegenerative disorders.

BACKGROUND OF THE INVENTION

Thrombin is an important serine protease in hemostasis and thrombosis. One of the key actions of thrombin is cellular modulation via receptor activation. A functional human thrombin receptor (PAR-1), cloned by Coughlin in 1991 (T.-K. Vu, Cell 1991, 64, 1057), was found to be a member of the G-protein coupled receptor (GPCR) superfamily. The receptor activation putatively occurs by N-terminal recognition and proteolytic cleavage at the Arg-41/Ser-42 peptide bond to reveal a truncated N-terminus. This new receptor sequence, which has an SFLLRN (Ser-Phe-Leu-Leu-Arg-Asn) N-terminus acting as a tethered ligand to recognize a site on the receptor, can trigger activation and signal transduction leading to platelet aggregation. Since 1991, three other protease-activated receptors with extensive homology to the thrombin receptor, "PAR-2" (S. Nystedt, Proc. Natl. Acad. Sci USA 1994, 91, 9208), "PAR-3" (H. Ishihara, Nature 1997, 386, 502), and "PAR-4" (W.-F. Xu, Proc. Natl. Acad. Sci USA 1998, 95, 6642), have been cloned. Thrombin receptor (PAR-1) specific antibody-induced blockade of the platelet thrombin receptor has shown efficacy against arterial thrombosis in vivo (J. J. Cook Circulation 1995, 91, 2961). Hence, antagonists of the thrombin receptor (PAR-1) are useful to block these protease-activated receptors and, as such, may be used to treat platelet mediated thrombotic disorders such as myocardial infarction, stroke, restenosis, angina, atherosclerosis, and ischemic conditions.

The thrombin receptor (PAR-1) has also been identified on other cell types: endothelial, fibroblast, renal, osteosarcoma, smooth muscle, myocytes, tumor, and neuronal/glia. Thrombin activation of endothelial cells upregulates P-selectin to induce polymorphonuclear leukocyte adhesion—an inflammatory response of the vessel wall (Y. Sugama, J. Cell Biol. 1992, 119, 935). In fibroblasts, thrombin receptor (PAR-1) activation induces proliferation and transmission of mitogenic signals (D. T. Hung, J. Cell Biol. 1992, 116, 827). Thrombin has been implicated in osteoblast proliferation through its activation of osteoblast cells (D. N. Tatakis, Biochem. Biophys. Res. Commun. 1991, 174, 181). Thrombin has been implicated in the regulation and retraction of neurons (K. Jalink, J. Cell. Biol. 1992, 118, 411). Therefore, in this context, the antagonist compounds of this invention may also be useful against inflammation, osteoporosis, Angiogenesis related disorders, cancer, neurodegenerative disorders, hypertension, heart failure, arrhythmia, glomerulonephritis.

The compounds of the present invention are a structurally novel class of indole peptidomimetics represented by the general formula (I) below.

SUMMARY OF THE INVENTION

The present invention is directed to structurally novel compounds represented by the following general formula (I):

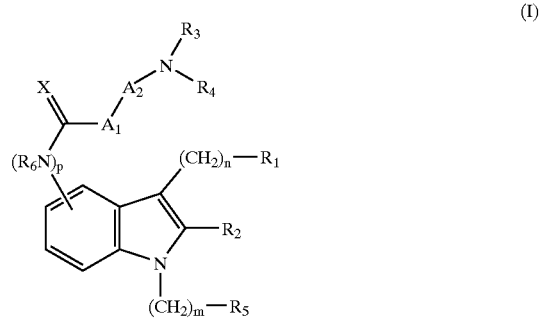

wherein:

$A_1$ and $A_2$ are each independently a D- or L-amino acid selected from the group consisting of alanine, β-alanine, arginine, homoarginine, cyclohexylalanine, citrulline, cysteine (optionally substituted with $C_1$–$C_4$ alkyl, aryl, or $arC_1$–$C_4$ alkyl), 2,4-diaminobutyric acid (optionally substituted with acyl, $C_1$–$C_4$ alkyl, aroyl, amidino, or MeC(NH)—), 2,3 diaminopropionic acid (optionally substituted with acyl, $C_1$–$C_4$ alkyl, aroyl, amidino, or MeC(NH)—), glutamine, glycine, indanylglycine, lysine (optionally substituted with acyl, $C_1$–$C_4$ alkyl, aroyl, MeC(NH)—), valine, methionine, proline, serine (optionally substituted with $C_1$–$C_4$ alkyl, aryl, or $arC_1$–$C_4$ alkyl), homoserine (optionally substituted with $C_1$–$C_4$ alkyl, aryl, or $arC_1$–C4 alkyl), tetrahydroisoquinoline-3-COOH, threonine (optionally substituted with $C_1$–$C_4$ alkyl, aryl, or $arC_1$–$C_4$ alkyl), ornithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, $arC_1$–$C_4$ alkyl, $C_2$–$C_4$ alkenyl, alkynyl, or nitro;

Preferably, $A_1$ and $A_2$ are each independently an L-amino acid selected from the group consisting of alanine, β-alanine, arginine, homoarginine, cyclohexylalanine, citrulline, cysteine (optionally substituted with $C_1$–$C_4$ alkyl, aryl, or $arC_1$-$C_4$ alkyl), 2,4-diaminobutyric acid (optionally substituted with acyl, $C_1$–$C_4$ alkyl, aroyl, amidino, or MeC(NH)—), 2,3 diaminopropionic acid (optionally substituted with acyl, $C_1$–$C_4$ alkyl, aroyl, amidino, or MeC(NH)—), glutamine, glycine, indanylglycine, lysine (optionally substituted with acyl, $C_1$–$C_4$ alkyl, aroyl, MeC(NH)—), valine, methionine, proline, serine (optionally substituted with $C_1$–$C_4$ alkyl, aryl, or $arC_1$–$C_4$ alkyl), homoserine (optionally substituted with $C_1$–$C_4$ alkyl, aryl, or $arC_1$–$C_4$ alkyl), tetrahydroisoquinoline-3-COOH, threonine (optionally substituted with $C_1$–$C_4$ alkyl, aryl, or $arC_1$–$C_4$ alkyl), ornithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$–$C_4$ alkyl. $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$R_1$ is selected from amino, $C_1$–$C_8$ alkylamino, $C_1$–$C_8$ dialkylamino, arylamino, ar$C_1$–$C_8$ alkylamino, $C_3$–$C_8$ cycloalkylamino, heteroalkyl$C_1$–$C_8$ alkylamino, heteroalkyl$C_1$–$C_8$ alkyl-N-methylamino, $C_1$–$C_8$ dialkylamino$C_1$–$C_8$ alkylamino, —N($C_1$–$C_8$alkyl)-$C_1$–$C_8$ alkyl-N($C_1$–$C_8$alkyl)$_2$, N($C_1$–$C_8$ alkyl)($C_1$–$C_8$ alkenyl), —N($C_1$–$C_8$alkyl)($C_3$–$C_8$cycloalkyl), heteroalkyl or substituted heteroalkyl wherein the substituent on the heteroalkyl is selected from oxo, amino, $C_1$–$C_8$ alkoxy$C_1$–$C_8$ alkyl, $C_1$–$C_8$ alkylamino or $C_1$–$C_8$ dialkylamino;

Preferably, $R_1$ is selected from amino, $C_1$–$C_6$ alkylamino, $C_1$–$C_6$ dialkylamino, arylamino, ar$C_1$–$C_6$ alkylamino, heteroalkyl$C_1$–$C_6$ alkylamino, —N($C_1$–$C_6$ alkyl)-$C_1$–$C_6$ alkyl-N($C_1$–$C_6$ alkyl)$_2$, heteroalkyl or substituted heteroalkyl wherein the substituent on the heteroalkyl is selected from oxo, amino, $C_1$–$C_6$ alkoxy $C_1$–$C_6$ alkyl, $C_1$–$C_6$ alkylamino or $C_1$–$C_6$ dialkylamino;

$R_2$ is selected from hydrogen, halogen, $C_1$–$C_8$ alkyl, $C_3$–$C_8$ cycloalkyl, $C_1$–$C_8$ alkenyl, $C_1$–$C_8$alkynyl, ar$C_1$–$C_8$alkyl, aryl or heteroaryl;

Preferably, $R_2$ is selected from hydrogen, halogen or phenyl;

$R_3$ and $R_4$ are each independently selected from hydrogen, $C_1$–$C_8$ alkyl, $C_3$–$C_8$ cycloalkyl, $C_3$–$C_8$ cycloalkyl$C_1$–$C_8$ alkyl, aryl, heteroalkyl, substituted heteroalkyl (wherein the substituent on the heteroalkyl is one or more substituents independently selected from $C_1$–$C_8$ alkoxycarbonyl, $C_1$–$C_8$ alkyl, or $C_1$–$C_4$ alkylcarbonyl), heteroalkyl$C_1$–$C_8$ alkyl, indanyl, acetamidino$C_1$–$C_8$ alkyl, amino$C_1$–$C_8$ alkyl, $C_1$–$C_8$ alkylamino$C_1$–$C_8$ alkyl, $C_1$–$C_8$ dialkylamino$C_1$–$C_8$ alkyl, unsubstituted or substituted heteroaryl$C_1$–$C_8$ alkyl, or unsubstituted or substituted ar$C_1$–$C_8$ alkyl, wherein the substituent on the aralkyl or heteroarylalkyl group is one or more substituents independently selected from halogen, nitro, amino, $C_1$–$C_8$ alkyl, $C_1$–$C_8$ alkoxy, hydroxy, cyano, $C_1$–$C_4$ alkylcarbonyl, $C_1$–$C_8$ alkoxycarbonyl, hydroxy$C_1$–$C_8$ alkyl or aminosulfonyl; or $R_3$ and $R_4$, together with the nitrogen to which they are attached, alternatively form an unsubstituted or substituted heteroalkyl group selected from piperidinyl, piperazinyl, morpholinyl or pyrrolidinyl, wherein the substituent is one or more substituents independently selected from $C_1$–$C_8$ alkyl $C_1$–$C_8$ alkoxycarbonyl or $C_1$–$C_4$alkylcarbonyl;

Preferably, $R_3$ is selected from hydrogen or $C_1$–$C_8$ alkyl;

$R_4$ is selected from $C_1$–$C_8$ alkyl, $C_3$–$C_6$ cycloalkyl, $C_3$–$C_6$ cycloalkyl$C_1$–$C_6$ alkyl, aryl, heteroaryl$C_1$–$C_6$ alkyl, substituted heteroaryl$C_1$–$C_6$ alkyl wherein the substituent is $C_1$–$C_4$ alkyl, heteroalkyl, heteroalkyl$C_1$–$C_6$ alkyl, indanyl, acetamidino$C_1$–$C_6$ alkyl, amino$C_1$–$C_8$ alkyl, $C_1$–$C_6$ alkylamino$C_1$–$C_6$ alkyl, $C_1$–$C_6$ dialkylamino$C_1$–$C_6$ alkyl, ar$C_1$–$C_8$ alkyl, substituted ar$C_1$–$C_8$ alkyl wherein the substituent on the aralkyl group is one to five substituents independently selected from halogen, nitro, amino, $C_1$–$C_6$ alkyl, $C_1$–$C_6$ alkoxy, $C_1$–$C_6$ alkoxycarbonyl, hydroxyalkyl or aminosulfonyl; or $R_3$ and $R_4$, together with the nitrogen to which they are attached, alternatively form an unsubstituted or substituted heteroalkyl group selected from piperidinyl, piperazinyl or pyrrolidinyl, wherein the substituent is independently one or two substituents selected from $C_1$–$C_6$ alkyl;

$R_3$ is selected from unsubstituted or substituted aryl, ar$C_1$–$C_8$ alkyl, $C_3$–$C_8$ cycloalkyl, or heteroaryl, where the substituents on the aryl, ar$C_1$–$C_8$ alkyl, cycloalkyl or heteroaryl group are independently selected from one or more of halogen, nitro, amino, cyano, hydroxyalkyl, $C_1$–$C_8$ alkyl, $C_1$–$C_8$ alkoxy, hydroxy, $C_1$–$C_4$ alkylcarbonyl, $C_1$–$C_8$ alkoxycarbonyl, fluorinated $C_1$–$C_4$ alkyl, fluorinated $C_1$–$C_4$ alkoxy or $C_1$–$C_4$ alkylsulfonyl;

Preferably, $R_5$ is selected from unsubstituted or substituted aryl, ar$C_1$–$C_6$ alkyl, $C_3$–$C_6$ cycloalkyl or heteroaryl, where the substituents on the aryl, aralkyl, cycloalkyl or heteroaryl group are independently selected from one to three substituents selected from halogen, cyano, $C_1$–$C_4$ alkyl, $C_1$–$C_4$ alkoxy, $C_1$–$C_4$ alkoxycarbonyl, fluorinated $C_1$–$C_4$ alkyl, fluorinated $C_1$–$C_4$ alkoxy or $C_1$–$C_4$ alkylsulfonyl;

$R_6$ is selected from hydrogen or $C_1$–$C_8$alkyl; preferably, $R_6$ is hydrogen;

X is oxygen or sulfur; preferably, X is oxygen;

m is an integer selected from 0, 1, 2 or 3;

n is an integer selected from 1 or 2;

p is an integer selected from 0 or 1; preferably, p is 1; and pharmaceutically acceptable salts thereof.

In a preferred embodiment of the present invention, wherein:

$A_1$ is an L-amino acid selected from the group consisting of alanine, arginine, cyclohexylalanine, glycine, proline, tetrahydroisoquinoline 3-COOH, and an unsubstituted or substituted aromatic amino acid selected from the group consisting of phenylalanine, naphthylalanine, homophenylalanine, and O-methyl tyrosine, wherein the substituents on the aromatic amino acid are independently selected from one to five of (preferably, one to three of) halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$A_2$ is an L-amino acid selected from the group consisting of alanine, β-alanine, arginine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3-diaminopropionic acid (optionally substituted with acyl, $C_1$–$C_4$ alkyl, aroyl, amidino, or MeC(NH)—), glutamine, glycine, lysine (optionally substituted with acyl, $C_1$–$C_4$ alkyl, aroyl, MeC(NH)—), valine, methionine, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), threonine (optionally substituted with $C_1$–$C_4$ alkyl, aryl, or ar$C_1$–$C_4$ alkyl), omithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, and histidine, wherein the substituents on the aromatic amino acid are independently selected from one to five of (preferably, one to three of) halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl ar$C_1$–$C_4$ alkyl, $C_2$–$C_4$ alkenyl, alkynyl, or nitro;

$R_2$ is selected from hydrogen, chlorine or phenyl;

$R_3$ is selected from hydrogen or $C_1$–$C_4$ alkyl;

m and n are both 1;
and all other variables are as defined previously; and pharmaceutically acceptable salts thereof.

In a class of the invention is a compound of the formula:

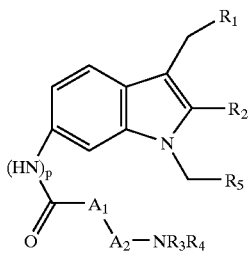

wherein:

$A_1$ is an L-amino acid selected from the group consisting of alanine, arginine, cyclohexylalanine, glycine, proline, and an unsubstituted or substituted aromatic amino acid selected from the group consisting of phenylalanine, naphthylalanine, homophenylalanine, and O-methyl tyrosine, wherein the substituents on the aromatic amino acid are independently one to two substituents selected from halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$A_2$ is an L-amino acid selected from the group consisting of alanine, β-alanine, arginine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3-diaminopropionic acid (optionally substituted with acyl, $C_1$–$C_4$ alkyl, aroyl, amidino, or MeC(NH)—), glutamine, glycine, lysine (optionally substituted with acyl, $C_1$–$C_4$ alkyl, aroyl, MeC(NH)—), valine, methionine, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, and histidine, wherein the substituents on the aromatic amino acid are independently one to two substituents selected from halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$R_1$ is selected from diethylamino, di-(n-propyl)amino,

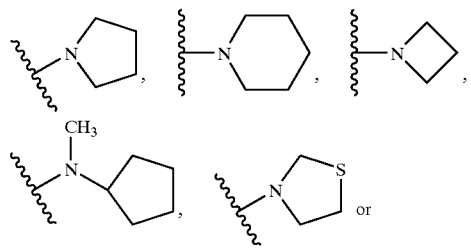

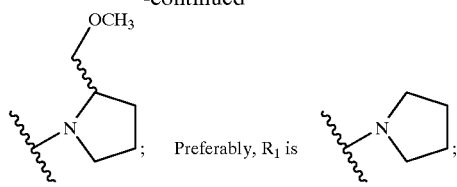

; Preferably, $R_1$ is $R_3$ is selected from hydrogen, methyl or ethyl;

$R_4$ is selected from 2-indanyl, phenyl, cyclohexylmethyl, cyclopentyl, pyridylmethyl, furanylmethyl, 2-(4-methylfuranyl)methyl, thienylmethyl, diphenylmethyl, 4-imidazolylethyl, 2-(4-N-methyl)imidazolylethyl, n-octyl, phenyl-n-propyl, aminoethyl, aminopropyl, amino-n-pentyl, dimethylaminoethyl, 4-aminophenylsulfonylaminomethyl, acetamidineylethyl, 2-N-pyrrolidinylethyl, N-ethoxycarbonylpiperidinyl, unsubstituted or substituted phenylethyl or unsubstituted or substituted benzyl wherein the substituents on the phenylethyl or benzyl are independently one or two substituents selected from methyl, fluorine, chlorine, nitro, methoxy, methoxycarbonyl or hydroxymethyl; or $R_3$ and $R_4$ together with the nitrogen to which they are attached, alternatively form a heteroalkyl group selected from piperidinyl or 4-(N-methyl)piperazinyl;

$R_6$ is selected from cyclohexyl, 2-naphthyl, phenylethyl, 4-fluorophenylethyl, or unsubstituted or substituted phenyl, where the substituents on the phenyl are independently selected from one to two substituents selected from fluorine, chlorine, iodine, methyl, cyano or trifluoromethyl;

Preferably, $R_5$ is 2,6-dichlorophenyl or 2-methylphenyl; and all other variables are as defined previously; and pharmaceutically acceptable salts thereof.

In a subclass of the invention, wherein:

$A_1$ is selected from 3,4-Difluorophenylalanine or 4-Chlorophenylalanine;

$A_2$ is selected from 2,4-Diaminobutyric acid or 4-Pyridylalanine;

$R_3$ is hydrogen;

$R_4$ is selected from benzyl or 2-aminoethyl;

and all other variables are as defined previously; and pharmaceutically acceptable salts thereof.

In another aspect of the invention is a compound of the formula (II):

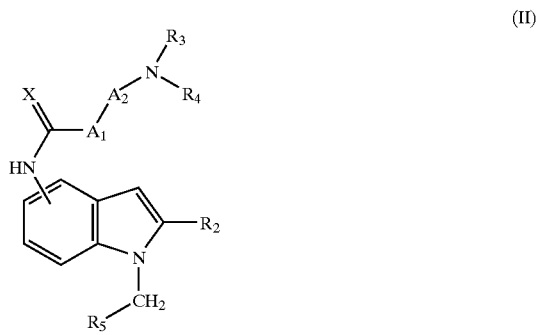

(II)

wherein:

$A_1$ and $A_2$ are each independently a D- or L-amino acid selected from the group consisting of alanine, β-alanine, arginine, homoarginine, cyclohexylalanine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3 diaminopropionic acid (optionally substituted with acyl, $C_1$–$C_4$ alkyl, aroyl, amidino, or MeC(NH)—), glutamine, glycine, indanylglycine, lysine (optionally substituted with acyl, $C_1$–$C_4$ alkyl, aroyl, MeC(NH)—), valine, methionine, proline, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), tetrahydroisoquinoline-3COOH, threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine, wherein the substituents on the aromatic amino acid are independently selected from one or more of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_6$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$R_2$ is selected from hydrogen, halogen, $C_1$–$C_8$ alkyl, $C_3$–$C_8$ cycloalkyl, $C_1$–$C_8$ alkenyl, $C_1$–$C_8$alkynyl, ar$C_1$–$C_8$ alkyl, aryl or heteroaryl;

$R_3$ and $R_4$ are each independently selected from hydrogen, $C_1$–$C_8$ alkyl, $C_3$–$C_8$ cycloalkyl, $C_3$–$C_8$ cycloalkyl$C_1$–$C_8$ alkyl, aryl, heteroalkyl, substituted heteroalkyl (wherein the substituent on the heteroalkyl is one or more substituents independently selected from $C_1$–$C_8$ alkoxycarbonyl, $C_1$–$C_8$ alkyl, or $C_1$–$C_4$ alkylcarbonyl), heteroalkyl$C_1$–$C_8$ alkyl, indanyl, acetamidino$C_1$–$C_8$ alkyl, amino$C_1$–$C_8$ alkyl, $C_1$–$C_8$ alkylamino$C_1$–$C_8$ alkyl, $C_1$–$C_8$ dialkylamino$C_1$–$C_8$ alkyl, unsubstituted or substituted heteroaryl$C_1$–$C_8$ alkyl, or unsubstituted or substituted ar$C_1$–$C_8$ alkyl, wherein the substituent on the aralkyl or heteroarylalkyl group is one or more substituents independently selected from halogen, nitro, amino, $C_1$–$C_8$ alkyl, $C_1$–$C_8$ alkoxy, hydroxy, cyano, $C_1$–$C_4$ alkylcarbonyl, $C_1$–$C_8$ alkoxycarbonyl, hydroxy$C_1$–$C_8$ alkyl or aminosulfonyl; or $R_3$ and $R_4$, together with the nitrogen to which they are attached, alternatively form an unsubstituted or substituted heteroalkyl group selected from piperidinyl, piperazinyl, morpholinyl or pyrrolidinyl, wherein the substituent is one or more substituents selected from $C_1$–$C_8$ alkyl $C_1$–$C_8$ alkoxycarbonyl or $C_1$–$C_4$ alkylcarbonyl;

$R_5$ is selected from unsubstituted or substituted aryl, ar$C_1$–$C_8$, alkyl, $C_3$–$C_8$ cycloalkyl or heteroaryl, where the substituents on the aryl, ar$C_1$–$C_8$ alkyl, cycloalkyl or heteroaryl group are independently selected from one or more of halogen, nitro, amino, cyano, hydroxyalkyl, $C_1$–$C_8$ alkyl, $C_1$–$C_8$ alkoxy, hydroxy, $C_1$–$C_4$ alkylcarbonyl, $C_1$–$C_4$ alkoxycarbonyl, fluorinated $C_1$–$C_4$ alkyl, fluorinated $C_1$–$C_4$ alkoxy or $C_1$–$C_4$ alkylsulfonyl; and, X is oxygen or sulfur; and salts thereof.

The invention is also directed to a process for preparing a compound of the formula (III):

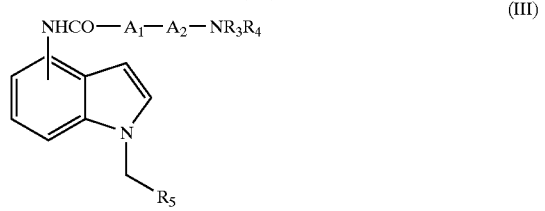

(III)

wherein:

$A_1$ and $A_2$ are each independently a D- or L-amino acid selected from the group consisting of alanine, β-alanine, arginine, homoarginine, cyclohexylalanine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3 diaminopropionic acid (optionally substituted with acyl, $C_1$–$C_4$ alkyl, aroyl, amidino, or MeC(NH)—), glutamine, glycine, indanylglycine, lysine (optionally substituted with acyl, $C_1$–$C_4$ alkyl, aroyl, MeC(NH)—), valine, methionine, proline, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), tetrahydroisoquinoline-3-COOH, threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine, wherein the substituents on the aromatic amino acid are independently selected from one or more of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$R_3$ and $R_4$ are each independently selected from hydrogen, $C_1$–$C_8$ alkyl, $C_3$–$C_8$ cycloalkyl, $C_3$–$C_8$ cycloalkyl$C_1$–$C_8$ alkyl, aryl, heteroalkyl, substituted heteroalkyl (wherein the substituent on the heteroalkyl is one or more substituents independently selected from $C_1$–$C_8$ alkoxycarbonyl, $C_1$–$C_8$ alkyl, or $C_1$–$C_4$ alkylcarbonyl), heteroalkyl$C_1$–$C_8$ alkyl, indanyl, acetamidino$C_1$–$C_8$ alkyl, amino$C_1$–$C_8$ alkyl, $C_1$–$C_8$ alkylamino$C_1$–$C_8$ alkyl, $C_1$–$C_8$ dialkylamino$C_1$–$C_8$ alkyl, unsubstituted or substituted heteroaryl$C_1$–$C_8$ alkyl or unsubstituted or substituted ar$C_1$–$C_8$ alkyl, wherein the substituent on the aralkyl or heteroarylalkyl group is one or more substituents independently selected from halogen, nitro, amino, $C_1$–$C_8$ alkyl, $C_1$–$C_8$ alkoxy, hydroxy, cyano, $C_1$–$C_4$ alkylcarbonyl, $C_1$–$C_8$ alkoxycarbonyl, hydroxy$C_1$–$C_8$ alkyl or aminosulfonyl; or $R_3$ and $R_4$, together with the nitrogen to which they are attached, alternatively form an unsubstituted or substituted heteroalkyl group selected from piperidinyl, piperazinyl, morpholinyl or pyrrolidinyl, wherein the substituent is one or more substituents independently selected from $C_1$–$C_8$ alkyl $C_1$–$C_8$ alkoxycarbonyl or $C_1$–$C_4$ alkylcarbonyl;

$R_5$ is selected from unsubstituted or substituted aryl, ar$C_1$–$C_8$ alkyl, $C_3$–$C_8$ cycloalkyl, or heteroaryl, where the substituents on the aryl, ar$C_1$–$C_8$ alkyl, cycloalkyl or heteroaryl group are independently selected from one or more of halogen, nitro, amino, cyano, hydroxyalkyl, $C_1$–$C_8$ alkyl, $C_1$–$C_8$ alkoxy, hydroxy, $C_1$–$C_4$ alkylcarbonyl, $C_1$–$C_8$ alkoxycarbonyl, fluorinated $C_1$–$C_4$ alkyl, fluorinated $C_1$–$C_4$ alkoxy or $C_1$–$C_4$ alkylsulfonyl; and, comprising reacting a compound of the formula (IV):

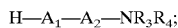

(IV)

with a compound of the formula (V):

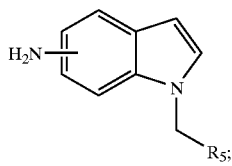

in the presence of a phosgene equivalent to form the compound of formula (III).

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

An example of the invention is a method of treating a disorder (preferably, a platelet-mediated thrombotic disorder) selected from arterial and/or venous thrombosis, acute myocardial infarction, reocclusion following thrombolytic therapy and/or angioplasty, inflammation, unstable angina, stroke, restenosis, athersclerosis, ischemic conditions, hypertension, heart failure, arrhythmia, glomerulonephritis, osteoporosis, Angiogenesis related disorders, cancer, neurodegenerative disorders or a variety of vaso-occlusive disorders in a subject in need thereof comprising administering to the subject a therapeutically effective amount of any of the compounds or pharmaceutical compositions described above. In a preferred embodiment, the therapeutically effective amount of the compound is from about 0.1 mg/kg/day to about 300 mg/kg/day.

Also included in the invention is the use of any of the compounds described above for the preparation of a medicament for a disorder (preferably, a platelet-mediated thrombotic disorder) selected from arterial and/or venous thrombosis, acute myocardial infarction, reocclusion following thrombolytic therapy and/or angioplasty, inflammation, unstable angina, stroke, restenosis, athersclerosis, ischemic conditions hypertension, heart failure, arrhythmia, glomerulonephritis, osteoporosis, Angiogenesis related disorders, cancer, neurodegenerative disorders or a variety of vaso-occlusive disorders in a subject in need thereof.

DETAILED DESCRIPTION OF THE INVENTION

More particularly, the present invention is directed to compounds of the following formula (I):

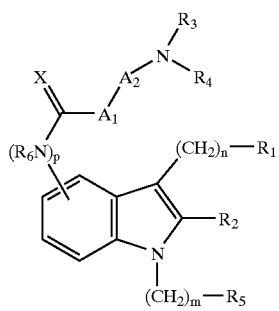

wherein $A_1$, $A_2$, $R_1$, $R_2$, $R_3$, $R_4$, $R_5$, X, m, n and p are as previously defined.

The compounds of the present invention are thrombin receptor antagonists and as such are useful in treating thrombosis, restenosis, hypertension, heart failure, arrhythmia, myocardial infarction, glomerulonephritis, reocclusion following thrombolytic therapy, reocclusion following angioplasty, inflammation, angina, stroke, atherosclerosis, Ischemic conditions, a vaso-occlusive disorder, neurodegenerative disorders, Angiogenesis related disorders and cancer. These compounds are also useful as antithrombotics in conjunction with fibrinolytic therapy (e.g., t-PA or streptokinase).

In the compounds of formula (I), the amino acid residues comprising the $A_1$ and $A_2$ substituents are attached to the adjacent moiety according to standard nomenclature so that the amino-terminus (N-terminus) of the amino acid is drawn on the left and the carboxy-terminus of the amino acid is drawn on the right. So, for example, in Compound 46, where $A_1$ is 3,4-difluorophenylalanine and $A_2$ is Arg, the N-terminus of the 3,4-difluorophenylalanine ($A_1$) is attached to the carbonylgroup and the carboxy-terminus of the 3,4-difluorophenylalanine ($A_1$) is attached to the N-terminus of the $A_2$ substituent (Arg), similarly, the the N-terminus of the Arg ($A_2$) is attached to the carboxy-terminus of the $A_1$ substituent and the carboxy-terminus of the Arg ($A_2$) is attached to the N—$R_3R_4$ group.

When a particular group is "substituted" (e.g., Phe, aryl, heteroalkyl, heteroaryl), that group may have one or more substituents, preferably from one to five substituents, more preferably from one to three substituents, most preferably from one to two substituents, independently selected from the list of substituents.

Under standard nomenclature used throughout this disclosure, the terminal portion of the designated side chain is described first, followed by the adjacent functionality toward the point of attachment. Thus, for example, a "phenyl$C_1$–$C_6$ alkylamido$C_1$–$C_6$alkyl" substituent refers to a group of the formula:

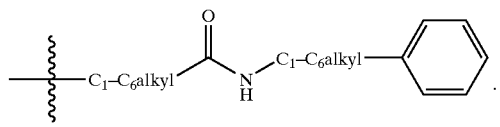

The compounds of the present invention may also be present in the form of a pharmaceutically acceptable salt. The pharmaceutically acceptable salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, unless otherwise noted alkyl and alkoxy whether used alone or as part of a substituent group, include straight and branched chains having 1 to 8 carbon atoms, or any number within this range. For example, alkyl radicals include methyl, ethyl, propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. Cycloalkyl groups contain 3 to 8 ring carbons and preferably 5 to 7 carbons. Similarly, alkenyl and alkynyl groups include straight and branched chain alkenes and alkynes having 1 to 8 carbon atoms or any number within this range.

The term "aryl" as used herein refers to an unsubstituted or substituted aromatic group such as phenyl and naphthyl. The term "aroyl" refers to the group —C(O)—aryl.

The term "heteroalkyl" as used herein represents an unsubstituted or substituted stable three to seven membered monocyclic saturated ring system which consists of carbon atoms and from one to three heteroatoms selected from N, O or S, and wherein the nitrogen or sulfur heteroatoms may optionally be oxidized, and the nitrogen heteroatom may optionally be quaternized. The heteroalkyl group may be attached at any heteroatom or carbon atom which results in the creation of a stable structure. Examples of such heteroalkyl groups include, but are not limited to azetidinyl, piperidinyl, pyrrolidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

Preferred heteroalkyl groups include pyrrolidinyl, piperidinyl, piperazinyl, morpholinyl, azetidinyl and tetrahydrothiazolyl.

The term "heteroaryl" as used herein represents an unsubstituted or substituted stable five or six membered monocyclic aromatic ring system or an unsubstituted or substituted nine or ten membered benzo-fused heteroaromatic ring system or bicyclic heteroaromatic ring system which consists of carbon atoms and from one to four heteroatoms selected from N, O or S, and wherein the nitrogen or sulfur heteroatoms may optionally be oxidized, and the nitrogen heteroatom may optionally be quaternized. The heteroaryl group may be attached at any heteroatom or carbon atom which results in the creation of a stable structure. Examples of heteroaryl groups include, but are not limited to pyridyl, pyridazinyl, thienyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl adeninyl or quinolinyl.

Preferred heteroaryl groups include pyridyl, pyrrolyl, pyrazinyl, thiadiazolyl, pyrazolyl, thienyl, triazolyl and quinolinyl.

The term "aralkyl" means an alkyl group substituted with one, two or three aryl groups (e.g., benzyl, phenylethyl, diphenylmethyl, triphenylmethyl). Similarly, the term "aralkoxy" indicates an alkoxy group substituted with an aryl group (e.g., benzyloxy). The term aminoalkyl refers to an alkyl group substituted with an amino group (i.e., -alkyl—NH$_2$). The term "alkylamino" refers to an amino group substituted with an alkyl group (i.e., —NH-alkyl). The term "dialkylamino" refers to an amino group which is disubstituted with alkyl groups wherein the alkyl groups can be the same or different (i.e., —N—[alkyl]$_2$).

The term "acyl" as used herein means an organic radical having 1 to 6 carbon atoms (branched or straight chain) derived from an organic acid by removal of the hydroxyl group.

The term "oxo" refers to the group=O.

The term "carbonyl" refers to the group C(O).

The term "halogen" shall include iodine, bromine, chlorine and fluorine.

The term "N(CH$_2$)$_4$" as used herein (e.g., in the Tables), refers to a pyrrolidinyl group having the structure:

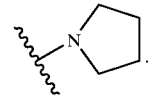

Similarly, "N(CH$_2$)$_5$", "N(CH$_2$)$_3$", "NCH$_2$S(CH$_2$)$_2$", and "N(CH$_2$)$_2$O(CH$_2$)$_2$" refer to:

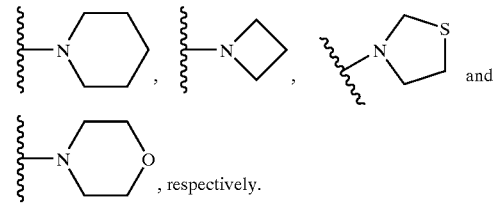

, respectively.

Similarly "C$_6$H$_{11}$" and "C$_5$H$_9$" (or "c—C$_6$H$_{11}$" and "c—C$_5$H$_9$") refer to cyclohexyl and cyclopentyl groups, respectively, and the term "D-Pro-ψ-CH$_2$OMe" refers to a group of the formula:

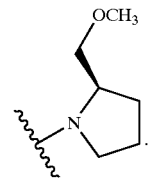

Whenever the term "alkyl" or "aryl" or either of their prefix roots appear in a name of a substituent (e.g., aralkyl, dialkylamino) it shall be interpreted as including those limitations given above for "alkyl" and "aryl." Designated numbers of carbon atoms (e.g., C$_1$–C$_6$) shall refer independently to the number of carbon atoms in an alkyl or cycloalkyl moiety or to the alkyl portion of a larger substituent in which alkyl appears as its prefix root.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

As used herein, the term "composition" is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention.

Amino add abbreviations are defined below:

| | |
|---|---|
| Ala | Alanine |
| β-Ala | beta-Alanine |
| Arg | Arginine |
| hArg | Homoarginine |
| Cha | Cyclohexylalanine |
| Cit | Citrulline |
| Cys | Cysteine |
| Dbu | 2,4-Diaminobutyric acid |
| Dpr | Diaminopropionic acid |
| Gln | Glutamine |

-continued

| | |
|---|---|
| Gly | Glycine |
| His | Histidine |
| Lys | Lysine |
| Met | Methionine |
| Nal | Naphthylalanine |
| Orn | Omithine |
| Phe | Phenylalanine |
| hPhe | Homophenylalanine |
| Pro | Proline |
| Pyr-Ala | Pyridylalanine |
| Ser | Serine |
| hSer | Homoserine |
| Tic | Tetrahydroisoquinoline-3-COOH |
| Tyr | Tyrosine |
| Val | Valine |

Particularly preferred compounds of the present invention are shown in Table 1 through Table 6, following; the amino acids bear the "L" absolute configuration unless denoted otherwise.

TABLE 1

6-Ureidoindoles

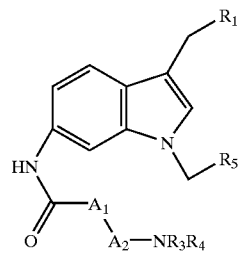

| Cpd No. | $R_1$ | $R_5$ | $A_1$ | $A_2$—$NR_3R_4$ | ES/MS (MH$^+$) |
|---|---|---|---|---|---|
| 1 | N(CH$_2$)$_4$ | 4-F—Ph | Tyr(Me) | Arg—NHBn | 790 |
| 2 | N(CH$_2$)$_4$ | 4-Me—Ph | Tyr(Me) | Arg—NHBn | 786 |
| 3 | NH c-C$_5$H$_9$ | 4-F—Ph | Tyr(Me) | Arg—NHBn | 804 |
| 4 | N(CH$_2$)$_4$ | 4-F—Ph | Tyr(Me) | Arg—NH(CH$_2$)$_3$Ph | 818 |
| 5 | NEt$_2$ | 4-F—Ph | Tyr(Me) | Arg—NH(CH$_2$)$_3$Ph | 820 |
| 6 | N(CH$_2$)$_4$ | 3-F—Ph | Tyr(Me) | Arg—NHBn | 790 |
| 7 | N(CH$_2$)$_4$ | 2-F—Ph | Tyr(Me) | Arg—NHBn | 790 |
| 8 | N(CH$_2$)$_5$ | 4-F—Ph | Tyr(Me) | Arg—NHCH$_2$C$_6$H$_{11}$ | 810 |
| 9 | N(CH$_2$)$_4$ | 3-Me—Ph | Tyr(Me) | Arg—NHCH$_2$C$_6$H$_{11}$ | 792 |
| 10 | N(CH$_2$)$_5$ | 4-CO$_2$Me—Ph | Tyr(Me) | Arg—NHCH$_2$C$_6$H$_{11}$ | 850 |
| 11 | N(CH$_2$)$_4$ | 4-OCF$_3$—Ph | Tyr(Me) | Arg—NHCH$_2$C$_6$H$_{11}$ | 862 |
| 12 | N(CH$_2$)$_4$ | 4-SO$_2$Me—Ph | Tyr(Me) | Arg—NHBn | 850 |
| 13 | N(CH$_2$)$_4$ | 4-CN—Ph | Tyr(Me) | Arg—NHBn | 797 |
| 14 | N(CH$_2$)$_4$ | 2,6-DiCl—Ph | Tyr(Me) | Arg—NHBn | 840 |
| 15 | N(CH$_2$)$_4$ | 2-Naphthalene | Tyr(Me) | Arg—NHBn | 822 |
| 16 | N(CH$_2$)$_4$ | 3-OMe—Ph | Tyr(Me) | Arg—NHBn | 802 |
| 17 | N(CH$_2$)$_4$ | 2-Me—Ph | Tyr(Me) | Arg—NHBn | 786 |
| 18 | N(CH$_2$)$_4$ | 4-CF$_3$—Ph | Tyr(Me) | Arg—NHBn | 840 |
| 19 | N(CH$_2$)$_4$ | 4-Cl—Ph | Tyr(Me) | Arg—NHBn | 806 |
| 20 | N(CH$_2$)$_4$ | 4-OMe—Ph | Tyr(Me) | Arg—NHBn | 802 |
| 21 | N(CH$_2$)$_4$ | 3,4-diF—Ph | Tyr(Me) | Arg—NHBn | 808 |
| 22 | N(CH$_2$)$_4$ | Ph | Tyr(Me) | Arg—NHBn | 772 |
| 23 | N(CH$_2$)$_4$ | 4-I—Ph | Tyr(Me) | Arg—NHBn | 898 |
| 24 | N(CH$_2$)$_4$ | 4-F—Ph | 4-Pyridyl-Ala | Arg—NHBn | 761 |
| 25 | N(CH$_2$)$_4$ | 4-F—Ph | Cha | Arg—NHBn | 766 |
| 26 | N(CH$_2$)$_4$ | 4-F—Ph | 4-F—Phe | Arg—NHBn | 778 |
| 27 | N(CH$_2$)$_4$ | 4-F—Ph | homoPhe | Arg—NHBn | 774 |
| 28 | N(CH$_2$)$_4$ | 4-F—Ph | 2-Thienyl-Ala | Arg—NHBn | 766 |
| 29 | N(CH$_2$)$_4$ | 2-Me—Ph | Phenyl-Gly | Arg—NHBn | 742 |
| 30 | N(CH$_2$)$_4$ | 4-F—Ph | Tic | Arg—NHBn | 772 |
| 31 | N(CH$_2$)$_4$ | 2-Me—Ph | 3-Pyridyl-Ala | Arg—NHBn | 757 |
| 32 | Nme(CH2)$_3$Nme$_2$ | 4-F—Ph | Tyr(Me) | Arg—NHBn | 835 |

TABLE 1-continued

6-Ureidoindoles

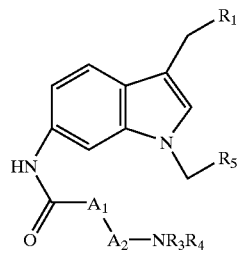

| Cpd No. | $R_1$ | $R_5$ | $A_1$ | $A_2$—$NR_3R_4$ | ES/MS (MH+) |
|---|---|---|---|---|---|
| 33 | $NH(CH_2)_3$—$N(CH_2)_4$ | 4-F—Ph | Tyr(Me) | Arg—NHBn | 847 |
| 34 | $N(CH_2)_4$ | 3-Me—Ph | Tyr(Allyl) | Arg—NHBn | 812 |
| 35 | $NEt_2$ | 2-Me—Ph | 4-$NH_2$—Phe | Arg—NHBn | 773 |
| 36 | $N(CH_2)_4$ | 2-Me—Ph | Tyr(Bn) | Arg—NHBn | 862 |
| 37 | $N(CH_2)_4$ | 2-Me—Ph | 1-Naphthyl-Ala | Arg—NHBn | 806 |
| 38 | $N(CH_2)_4$ | 2,6-DiCl—Ph | 2-Naphthyl-Ala | Arg—NHBn | 860 |
| 39 | $N(CH_2)_4$ | 2-Me—Ph | 4-Ph—Phe | Arg—NHBn | 832 |
| 40 | $N(CH_2)_2O(CH_2)_2$ | 4-F—Ph | Tyr(Me) | Arg—NHBn | 806 |
| 41 | N-(n-Pr)$_2$ | 2,6-DiCl—Ph | Tyr(Me) | Arg—NHBn | 870 |
| 42 | $N(CH_2)_4$ | 3-Me—Ph | Tyr(Et) | Arg—NHBn | 800 |
| 43 | $NEt_2$ | 3-Me—Ph | Tyr(i-Pr) | Arg—NHBn | 816 |
| 44 | $N(CH_2)_3$ | 4-F—Ph | Tyr(Me) | Arg—NHBn | 776 |
| 45 | NH-o-$C_3H_5$ | 4-F—Ph | Tyr(Me) | Arg—NHBn | 776 |
| 46 | $N(CH_2)_4$ | 2,6-DiCl—Ph | 3,4-DiF—Phe | Arg—NHBn | 847 |
| 47 | $N(CH_2)_4$ | 2,6-DiCl—Ph | 3-F—Phe | Arg—NHBn | 828 |
| 48 | $N(CH_2)_4$ | 2-Me—Ph | 4-Cl—Phe | Arg—NHBn | 790 |
| 49 | $N(CH_2)_4$ | 4-F—Ph | 4-$NO_2$—Phe | Arg—NHBn | 805 |
| 50 | $N(CH_2)_4$ | 2-Me—Ph | penta-F—Phe | Arg—NHBn | 846 |
| 51 | $N(CH_2)_4$ | 2,6-DiCl—Ph | 2-F—Phe | Arg—NHBn | 828 |
| 52 | $N(CH_2)_4$ | 2,6-DiCl—Ph | 4-CN—Phe | Arg—NHBn | 835 |
| 53 | $N(CH_2)_4$ | 2,6-DiCl—Ph | 4-Thiazolyl-Ala | Arg—NHBn | 817 |
| 54 | $N(CH_2)_4$ | 2-Me—Ph | 3-$CF_3$—Phe | Arg—NHBn | 824 |
| 55 | $N(CH_2)_4$ | 2-Cl—Ph | 3,4-DiF—Phe | Arg—NHBn | 812 |
| 56 | $N(CH_2)_4$ | 2,6-DiCl—Ph | DiPh—Ala | Arg—NHBn | 886 |
| 57 | $N(CH_2)_4$ | 2-Me—Ph | 3,4-DiF—Phe | Arg—$NH(CH_2)_2Ph$ | 806 |
| 58 | N-(n-Bu)$_2$ | 2-Me—Ph | 3,5-DiF—Phe | Arg—NHBn | 850 |
| 59 | $N(CH_2)_4$ | 2,6-DiCl—Ph | 3,4-DiF—Phe | Arg—NH-4-F—Bn | 864 |
| 60 | $N(CH_2)_4$ | 4-F—Ph | 3,4-DiF—Phe | Arg—NH—$CHPh_2$ | 872 |
| 61 | $N(CH_2)_4$ | 2,6-DiCl—Ph | 3,4-DiF—Phe | Arg—NH-4-MeO—Bn | 876 |
| 62 | $N(CH_2)_4$ | 2,6-DiCl—Ph | 3,4-DiF—Phe | Arg—$NHCH_2$-4-pyridyl | 847 |
| 63 | $N(CH_2)_5$ | 2,6-DiCl—Ph | 4-Br—Phe | Arg—NHBn | 902 |
| 64 | $N(CH_2)_4$ | 2-Me—Ph | 3,4-DiF—Phe | Arg—NH—$(CH_2)_2$-2-Cl—Ph | 840 |
| 65 | $N(CH_2)_4$ | 2-Me—Ph | 3,4-DiF—Phe | Arg—NH—$(CH_2)_2$-2-MeO—Ph | 836 |
| 66 | $N(CH_2)_4$ | 2,6-DiCl—Ph | 3,4-DiF—Phe | Orn—NHBn | 804 |
| 67 | $N(CH_2)_5$ | 2,6-DiCl—Ph | 3,4-DiF—Phe | Lys(iPr)—NHBn | 874 |
| 68 | $N(CH_2)_4$ | 2,6-DiCl—Ph | 3,4-DiF—Phe | Lys(3-Pyridyl-CO)—NHBn | 923 |
| 69 | $N(CH_2)_4$ | 2,6-DiCl—Ph | 3,4-DiF—Phe | D-Arg—NHBn | 846 |
| 70 | $N(CH_2)_4$ | 2,6-DiCl—Ph | 3,4-DiF—Phe | Lys—NHBn | 818 |
| 71 | $N(CH_2)_4$ | 2,6-DiCl—Ph | 3,4-DiF—Phe | Lys(Ac)—NHBn | 860 |
| 72 | $N(CH_2)_4$ | 2,6-DiCl—Ph | 3,4-DiF—Phe | His—NHBn | 827 |
| 73 | $N(CH_2)_5$ | 4-F—Ph | 3,4-DiF—Phe | Arg—NH—$(CH_2)_7$Me | 832 |
| 74 | $N(CH_2)_4$ | o-$C_6H_{11}$ | 3,4-DiF—Phe | Arg—NHBn | 784 |
| 75 | $NEt_2$ | $(CH_2)_2$—Ph | 3,4-DiF—Phe | Arg—NHBn | 808 |
| 76 | $NEt_2$ | $CH_2$-4-F—Ph | 3,4-DiF—Phe | Arg—NHBn | 812 |
| 77 | $N(CH_2)_4$ | 2,6-DiCl—Ph | 3-F—Phe | Cit—NHBn | 829 |
| 78 | $N(CH_2)_4$ | 2,6-DiCl—Ph | 4-Cl—Phe | Dbu—NHBn | 788 |
| 79 | $N(CH_2)_4$ | 2,6-DiCl—Ph | 4-Cl—Phe | Dpr—NHBn | 774 |
| 80 | $N(CH_2)_4$ | 2,6-DiCl—Ph | Arg | 3,4-DiF—Phe—NHBn | 846 |
| 81 | $N(CH_2)_4$ | 2,6-DiCl—Ph | 3,4-DiF—Phe | Arg—NH—$(CH_2)_5$—$NH_2$ | 841 |
| 82 | $N(CH_2)_4$ | 4-F—Ph | 3,4-DiF—Phe | Arg—$NHCH_2$-2-furanyl | 786 |
| 83 | $N(CH_2)_4$ | 2,6-DiCl—Ph | 3,4-DiF—Phe | Arg—NH—$CH_2$—[R—CH(Me)Ph] | 874 |
| 84 | $N(CH_2)_4$ | 2,6-DiCl—Ph | D-3,4-DiF—Phe | Arg—NHBn | 846 |
| 85 | $N(CH_2)_5$ | 2,6-DiCl—Ph | 4-I—Phe | Arg—NHBn | 950 |
| 86 | $N(CH_2)_5$ | 2,6-DiCl—Ph | 2-Cl—Phe | Arg—NHBn | 858 |
| 87 | D-Pro-ψ-$CH_2$OMe | 2,6-DiCl—Ph | 4-Cl—Phe | Arg—NHBn | 888 |
| 88 | $N(CH_2)_2CO(CH_2)_2$ | 2,6-DiCl—Ph | 3-F—Phe | Arg—NHBn | 856 |
| 89 | $N(CH_2)_4$ | 4-F—Ph | 3-F—Phe | Arg—NH-2-naphthyl | 828 |
| 90 | $NCH_2CH(NMe_2)(CH_2)_2$ | 2-Me—Ph | D-3,4-DiF—Phe | Arg—NHBn | 835 |
| 91 | D-Pro-ψ-$CH_2$OMe | 2,6-DiCl-4-Pyr | 3-F—Phe | Arg—NHBn | 873 |
| 92 | $N(CH_2)_4$ | 2,6-DiCl—Ph | 3-F—Phe | Arg—$NHCH_2$-4-$NH_2SO_2$—Ph | 907 |

TABLE 1-continued

6-Ureidoindoles

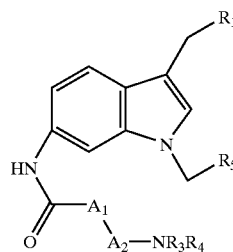

| Cpd No. | R₁ | R₅ | A₁ | A₂—NR₃R₄ | ES/MS (MH⁺) |
|---|---|---|---|---|---|
| 93 | N(CH₂)₄ | 2,6-DiCl—Ph | 3,4-DiF—Phe | Orn—OCH₂CHCH₂ | 755 |
| 94 | N(CH₂)₄ | 2,6-DiCl—Ph | 3,4-DiF—Phe | Orn(Ac)—NHBn | 846 |
| 95 | N(CH₂)₄ | 2,6-DiCl—Ph | 3,4-DiF—Phe | Orn[(MeC(NH)]—NHBn | 845 |
| 96 | N(CH₂)₄ | 2,6-DiCl—Ph | 3-F—Phe | Orn—NH-2-indanyl | 812 |
| 97 | N(Me)CH₂CH=CH₂ | 2,6-DiCl—Ph | 3-F—Phe | Orn—NH-2-indanyl | 812 |
| 98 | N(CH₂)₄ | 2,6-DiCl—Ph | 3,4-DiF—Phe | Orn—NHCH₂-4-pyridyl | 805 |
| 99 | N(CH₂)₄ | 2,6-DiCl—Ph | 4-Cl—Phe | Orn—NHCH₂-2-Cl—Ph | 836 |
| 100 | N(CH₂)₄ | 2,6-DiCl—Ph | 3,4-DiF—Phe | Orn(Me₂)—NHBn | 832 |
| 101 | N(CH₂)₄ | 2,6-DiCl—Ph | 3,4-DiF—Phe | Dpr—NHBn | 776 |
| 102 | N(CH₂)₄ | 2,6-DiCl—Ph | 3,4-DiF—Phe | Dbu—NHBn | 790 |
| 103 | N(CH₂)₄ | 2,6-DiCl—Ph | 3,4-DiF—Phe | Gln—NHBn | 818 |
| 104 | N(CH₂)₄ | 2,6-DiCl—Ph | 3,4-DiF—Phe | Met—NHBn | 821 |
| 105 | N(CH₂)₄ | 2,6-DiCl—Ph | 3,4-DiF—Phe | 4-Pyridyl-Ala—NHBn | 838 |
| 106 | N(CH₂)₄ | 2,6-DiCl—Ph | 3,4-DiF—Phe | 4-NH₂—Phe—NHBn | 852 |
| 107 | N(CH₂)₄ | 2,6-DiCl—Ph | Pro | Arg—NHBn | 760 |
| 108 | N(CH₂)₄ | 2,6-DiCl—Ph | 3,4-DiF—Phe | β-Ala—Arg—NHBn | 917 |
| 109 | N(CH₂)₄ | 2,6-DiCl—Ph | 3,4-DiF—Phe | Orn—NH(CH₂)₂-4-pyridyl | 819 |
| 110 | N(CH₂)₄ | 2,6-DiCl—Ph | 3,4-DiF—Phe | Orn—N(Et)—CH₂-4-pyridyl | 833 |
| 111 | N(CH₂)₄ | 2,6-DiCl—Ph | 3,4-DiF—Phe | Orn—N(Me)—CH₂Ph | 818 |
| 112 | N(CH₂)₄ | 2,6-DiCl—Ph | 3,4-DiF—Phe | Orn—NH-3,4-DiCl—Bn | 872 |
| 113 | N(CH₂)₄ | 2,6-DiCl—Ph | 3,4-DiF—Phe | Orn—NH—CH₂-2-thienyl | 810 |
| 114 | N(CH₂)₄ | 2,6-DiCl—Ph | 3,4-DiF—Phe | Orn-4-N—Me-piperazinyl | 797 |
| 115 | N(CH₂)₄ | 2,6-DiCl—Ph | 3,4-DiF—Phe | Orn-piperidinyl | 782 |
| 116 | N(CH₂)₄ | 2,6-DiCl—Ph | 3,4-DiF—Phe | Orn—NHCH₂-3-pyridyl | 805 |
| 117 | N(CH₂)₄ | 2,6-DiCl—Ph | 3,4-DiF—Phe | Orn—NHCH₂-2-pyridyl | 805 |
| 118 | N(CH₂)₄ | 2,6-DiCl—Ph | 3,4-DiF—Phe | Dbu[(MeC(NH)]—NHBn | 831 |
| 119 | N(Me)-c-C₅H₉ | 2,6-DiCl—Ph | 4-Cl—Phe | Orn—NH—(CH₂)₂-2-Cl—Ph | 878 |
| 120 | NH(CH₂)₂—NMe₂ | 2,6-DiCl—Ph | 3,4-DiF—Phe | Orn—NH-2-indanyl | 861 |
| 121 | NH(CH₂)₃—NMe₂ | 2,6-DiCl—Ph | 3,4-DiF—Phe | Orn—NH-2-indane | 875 |
| 122 | N(Me)—CH₂-2-dioxolanyl | 2,6-DiCl—Ph | 4-Cl—Phe | Orn—NH-2-indane | 874 |
| 123 | N(CH₂)₄ | 2,6-DiCl—Ph | 4-Cl—Phe | Orn—NH(CH₂)₂—N-morpholinyl | 839 |
| 124 | N(CH₂)₄ | 2,6-DiCl—Ph | 3,4-DiF—Phe | Orn—NH(CH₂)₂-4-(N—Me)imidazolyl | 822 |
| 125 | N(CH₂)₄ | 2,6-DiCl—Ph | 3,4-DiF—Phe | OrnNH-c-C₅H₉ | 782 |
| 126 | N(CH₂)₄ | 2,6-DiCl—Ph | 3,4-DiF—Phe | Orn—NH(CH₂)₂—NMe₂ | 785 |
| 127 | N(CH₂)₄ | 2,6-DiCl—Ph | 3,4-DiF—Phe | Orn—NH—Ph | 790 |
| 128 | N(CH₂)₄ | 2,6-DiCl—Ph | hPhe | Dbu—NHBn | 768 |
| 129 | N(CH₂)₄ | 2,6-DiCl—Ph | 2-Nal | Dbu—NHBn | 804 |
| 130 | N(CH₂)₄ | 2,6-DiCl—Ph | 3-Pyridyl-Ala | Dbu—NHBn | 755 |
| 131 | N(CH₂)₄ | 2,6-DiCl—Ph | 2-Thienyl-Ala | Dbu—NHBn | 760 |
| 132 | N(CH₂)₄ | 2,6-DiCl—Ph | 4-Thiazolyl-Ala | Dbu—NHBn | 761 |
| 133 | N(CH₂)₄ | 2,6-DiCl—Ph | 4-Cl—Phe | Phe—NH(CH₂)₂—NH₂ | 788 |
| 134 | N(CH₂)₄ | 2,6-DiCl—Ph | 4-Cl—Phe | His—NH(CH₂)₂NH₂ | 776 |
| 135 | N(CH₂)₄ | 2,6-DiCl—Ph | 4-Cl—Phe | 4-Pyr—Ala—NH(CH₂)₂NH₂ | 789 |
| 136 | N(CH₂)₄ | 2,6-DiCl—Ph | 4-Cl—Phe | 2-Thienyl-Ala—NH(CH₂)₂NH₂ | 794 |
| 137 | N(CH₂)₄ | 2,6-DiCl—Ph | 4-Cl—Phe | 4-Thiazolyl-AlaNH(CH₂)₂NH₂ | 795 |
| 138 | N(CH₂)₄ | 2,6-DiCl—Ph | 3,4-DiF—Phe | 3-F—Phe—NH(CH₂)₂NH₂ | 808 |
| 139 | N(CH₂)₄ | 2,6-DiCl—Ph | 4-Cl—Phe | 4-Pyr—AlaNH(CH₂)₂NHC(NH)Me | 830 |
| 140 | N(CH₂)₄ | 2,6-DiCl—Ph | 3,4-DiF—Phe | Dbu[C(NH)Me]—NH(CH₂)₂NHC(NH)Me | 825 |
| 141 | N(CH₂)₄ | 2,6-DiCl—Ph | 3,4-DiF—Phe | Dbu—NH(CH₂)₂—N-pyrrolidinyl | 797 |
| 142 | N(CH₂)₄ | 2,6-DiCl—Ph | 3,4-DiF—Phe | Dbu—NH(CH₂)₂-4-imidazolyl | 794 |
| 143 | N(CH₂)₄ | 2,6-DiCl—Ph | 3,4-DiF—Phe | Met—NH(CH₂)₂NH₂ | 774 |
| 144 | N(CH₂)₄ | 2,6-DiCl—Ph | 3,4-DiF—Phe | Dbu-4-NH—N—CO₂Et-piperidinyl | 855 |
| 145 | N(CH₂)₄ | 2,6-DiCl—Ph | 4-Cl—Phe | 4-Pyr—Ala—NH(CH₂)₃NH₂ | 803 |
| 146 | N(CH₂)₄ | 2,6-DiCl—Ph | 4-Cl—Phe | β-Ala—NH(CH₂)₂NH₂ | 712 |
| 147 | N(CH₂)₄ | 2,6-DiCl—Ph | 3-F—Phe | Gly—NH(CH₂)₂NH₂ | 682 |
| 148 | N(CH₂)₄ | 2,6-DiCl—Ph | 4-Cl—Phe | Val—NH(CH₂)₂NH₂ | 740 |
| 149 | N(CH₂)₄ | 2,6-DiCl—Ph | 4-Cl—Phe | Cys(Et)—NH(CH₂)₂NH₂ | 772 |
| 150 | N(CH₂)₄ | 2,6-DiCl—Ph | 3,4-DiF—Phe | Ser—NH(CH₂)₂NH₂ | 730 |
| 151 | N(CH₂)₄ | 2,6-DiCl—Ph | 3,4-DiF—Phe | Cys(Tr)—NH(CH₂)₂NH₂ | 989 |

TABLE 1-continued

6-Ureidoindoles

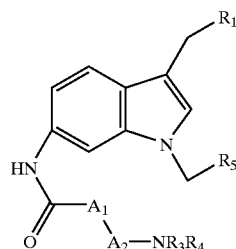

| Cpd No. | R$_1$ | R$_5$ | A$_1$ | A$_2$—NR$_3$R$_4$ | ES/MS (MH$^+$) |
|---|---|---|---|---|---|
| 152 | N(CH$_2$)$_4$ | 2,6-DiCl—Ph | D-4-Cl—Phe | D-2Thienyl-Ala—NH(CH$_2$)$_2$NH$_2$ | 779 |
| 153 | N(CH$_2$)$_4$ | 3-Me—Ph | 3,4-DiF—Phe | 2-Thienyl-Ala—NH(CH$_2$)$_3$NH$_2$ | 756 |
| 154 | NCH$_2$S(CH$_2$)$_2$ | 2,6-DiCl—Ph | 3,4-DiF—Phe | Dbu—NHBn | 808 |
| 155 | N(CH$_2$)$_4$ | 2,6-DiCl—Ph | Cha | Dbu—NHBn | 760 |
| 156 | N(CH$_2$)$_4$ | 2,6-DiCl—Ph | 3,4-DiF—Phe | hSer(Me)—NH(CH$_2$)$_2$NH$_2$ | 758 |
| 157 | N(CH$_2$)$_4$ | 2,6-DiCl—Ph | 3,4-DiF—Phe | Dbu—NH—[R—CH(Me)Ph] | 803 |
| 158 | N(CH$_2$)$_4$ | 2,6-DiCl—Ph | 3,4-DiF—Phe | Dbu—NH-4-NO$_2$—Bn | 834 |
| 159 | N(CH$_2$)$_4$ | 2,6-DiCl—Ph | 3,4-DiF—Phe | Dbu—NHCH$_2$-2-(4-Me-furanyl) | 793 |
| 160 | N(CH$_2$)$_4$ | 2,6-DiCl—Ph | 3,4-DiF—Phe | Dbu—NH—[S—CH(CO$_2$Me)Ph] | 847 |
| 161 | N(CH$_2$)$_4$ | 2,6-DiCl—Ph | 3,4-DiF—Phe | Dbu—NH—[S—CH(CH$_2$OH)Ph] | 819 |

TABLE 2

5-Ureidoindoles

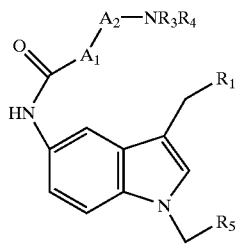

| Cpd No. | R$_1$ | R$_5$ | A$_1$ | A$_2$—NR$_3$R$_4$ | ES/MS (MH$^+$) |
|---|---|---|---|---|---|
| 162 | N(CH$_2$)$_5$ | 4-F—Ph | Tyr(Me) | Arg—NHBn | 804 |
| 163 | NCH$_2$SCH$_2$CH$_2$ | 4-F—Ph | Tyr(Me) | Arg—NHBn | 808 |
| 164 | N(CH$_2$)$_4$ | 4-F—Ph | 3,4-DiF—Phe | Dbu—NHBn | 740 |

TABLE 3

4-Ureidoindoles

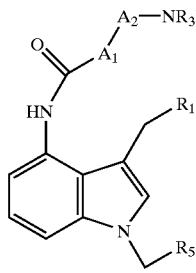

| Cpd No | R$_1$ | R$_5$ | A$_1$ | A$_2$—NR$_3$R$_4$ | ES/MS (MH$^+$) |
|---|---|---|---|---|---|
| 165 | N(CH$_2$)$_4$ | 2,6-DiCl—Ph | 3,4-DiF—Phe | Dbu—NHBn | 790 |
| 166 | N(CH$_2$)$_4$ | 2,6-DiCl—Ph | 3,4-DiF—Phe | Dbu—NH(CH$_2$)$_2$—N(CH$_2$)$_4$ | 797 |

TABLE 4

7-Ureidoindoles

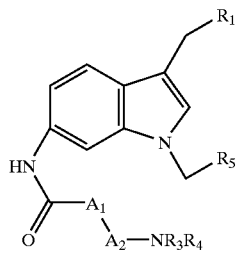

| Cpd No | R₁ | R₅ | A₁ | A₂—NR₃R₄ | ES/MS (MH⁺) |
|---|---|---|---|---|---|
| 167 | N(CH₂)₄ | 2,6-DiCl—Ph | 3,4-DiF—Phe | Dbu—NHBn | 790 |
| 168 | N(CH₂)₄ | 2-Me—Ph | 3,4-DiF—Phe | Dbu—NHBn | 736 |
| 169 | N(CH₂)₄ | 2-Me—Ph | 3,4-DiF—Phe | Dbu—NH(CH₂)₄ | 743 |
| 170 | N(CH₂)₄ | 2,6-DiCl—Ph | 3,4-DiF—Phe | Dbu—NH(CH₂)₄ | 797 |

TABLE 5

2-Substituted 6-Ureidoindoles

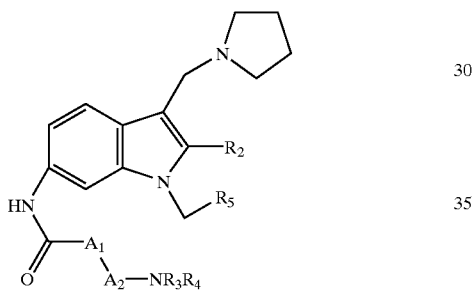

| Cpd No | R₂ | R₅ | A₁ | A₂—NR₃R₄ | ES/MS (MH⁺) |
|---|---|---|---|---|---|
| 171 | Ph | 4-F—Ph | 3,4-DiF—Phe | Arg—NH-4-F—Bn | 890 |
| 172 | Cl | 2-Me—Ph | 3,4-DiF—Phe | Arg—NHBn | 826 |
| 173 | Cl | 2-Me—Ph | 3-F—Phe | Arg—NH-4-F—Bn | 826 |

TABLE 6

6-Amidoindoles

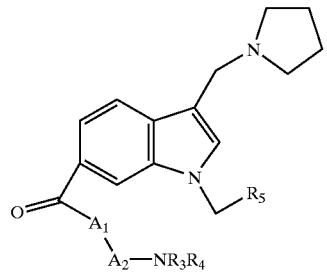

| Cpd No | R₅ | A₁ | A₂—NR₃R₄ | ES/MS (MH⁺) |
|---|---|---|---|---|
| 174 | 4-Me—Ph | Tyr(Me) | Arg—NHBn | 771 |
| 175 | 2,6-DiCl—Ph | 3,4-DiF—Phe | 4-Pyr—Ala—NH(CH₂)₂NH₂ | 776 |

TABLE 6-continued

6-Amidoindoles

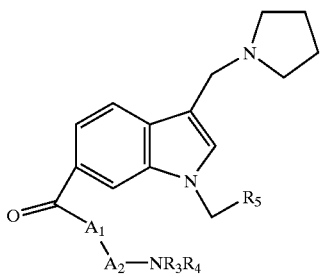

| Cpd No | $R_5$ | $A_1$ | $A_2$—$NR_3R_4$ | ES/MS (MH+) |
|---|---|---|---|---|
| 176 | 2,6-DiCl—Ph | D-3,4-DiF—Phe | D-4-Pyr—Ala—NH(CH$_2$)$_2$NH$_2$ | 776 |
| 177 | 2,6-DiCl—Ph | 4-Cl—Phe | 2-Thienyl-Ala—NH(CH$_2$)$_2$NH$_2$ | 779 |
| 178 | 2,6-DiCl—Ph | D-4-Cl—Phe | D-2-Thienyl-Ala—NH(CH$_2$)$_2$NH$_2$ | 779 |

The antagonists of the present invention may be prepared via either solution-phase or solid-phase methods. All compounds presented in Table 1 through Table 4 may be prepared by a convergent solution-phase synthesis as described in the general Scheme AAGeneric. A typical example was represented by the synthesis of Compound 46 (Scheme AA). Alternatively, compounds in Tables 1 through Table 4 can also be prepared via solid-phase approaches as represented by the synthesis of Compound 102 and Compound 135 (Schemes AB and AC). The antagonists in Table 5 and Table 6 can be prepared by using the methods as described in Schemes AD and AE.

The appropriately nitro substituted indole AAG1 (Scheme AAGeneric) was alkylated with a substituted aralkyl or heteroaryl alkyl halide and a base such as cesium or potassium carbonate in a dipolar aprotic solvent such as DMF to give an intermediate, which was reduced in a classical manner with for example iron and acetic acid or with a newer method such as dimethyl hydrazine and iron to give AAG2.

An Fmoc protected amino-acid ($A_2$), AAG3 (Scheme AAGeneric), was coupled to amine $R_3R_4NH$ using a coupling agent such as dicyclohexylcarbodiimide (DCC) or diisopropylcarbodiimide (DIC) and 1-hydroxybenzotriazole (HOBT) in a dipolar aprotic solvent such as DMF to give the amide, which was Fmoc deprotected with a dialkylamine in a dipolar aprotic solvent—such as diethylamine in acetonitrile. This amine was coupled to the second Fmoc protected amino-acid ($A_1$) in the same way with a coupling agent such as DIC and HOBT in a dipolar aprotic solvent such as DMF to give the dipeptide, which was deprotected as above with a dialkylamine in a dipolar aprotic solvent such as acetonitrile to afford the dipeptide amine AAG4. Amine AAG2 was treated with a phosgene equivalent such as 4-nitrophenyl chloroformate, phosgene or "COCl$_2$," phenyl chloroformate, triphosgene or "(CCl$_3$O)$_2$CO," carbonyldiimidazole, diethyl carbonate or diphenyl carbonate and a base such as diisopropylethylamine in a solvent such as dichloromethane to which was then added the dipeptide intermediate AAG4 to give the urea AAG5. The indole intermediate AAG5 was combined with formaldehyde, an amine such as pyrrolidine and an acid such as acetic acid, either neat or diluted with another solvent such as 1,4-dioxane or tetrahydrofuran. Upon work-up and deprotection with an acid, if necessary such as trifluoroacetic acid, the target product AAG6 was obtained.

SCHEME AAGeneric

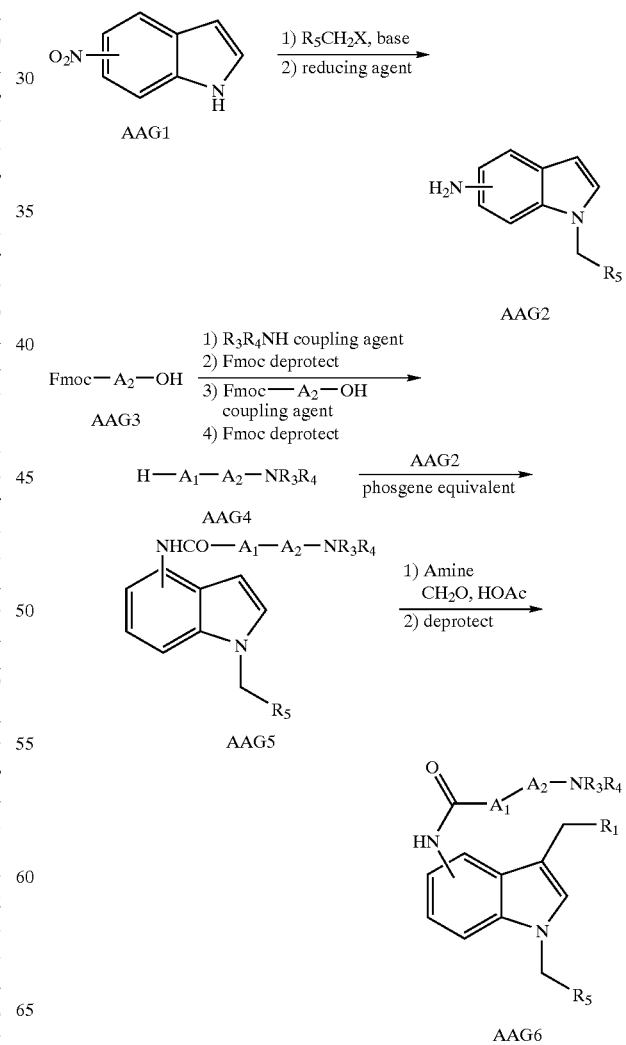

Scheme AA presents a typical example of the convergent solution-phase synthesis of Compound 46.
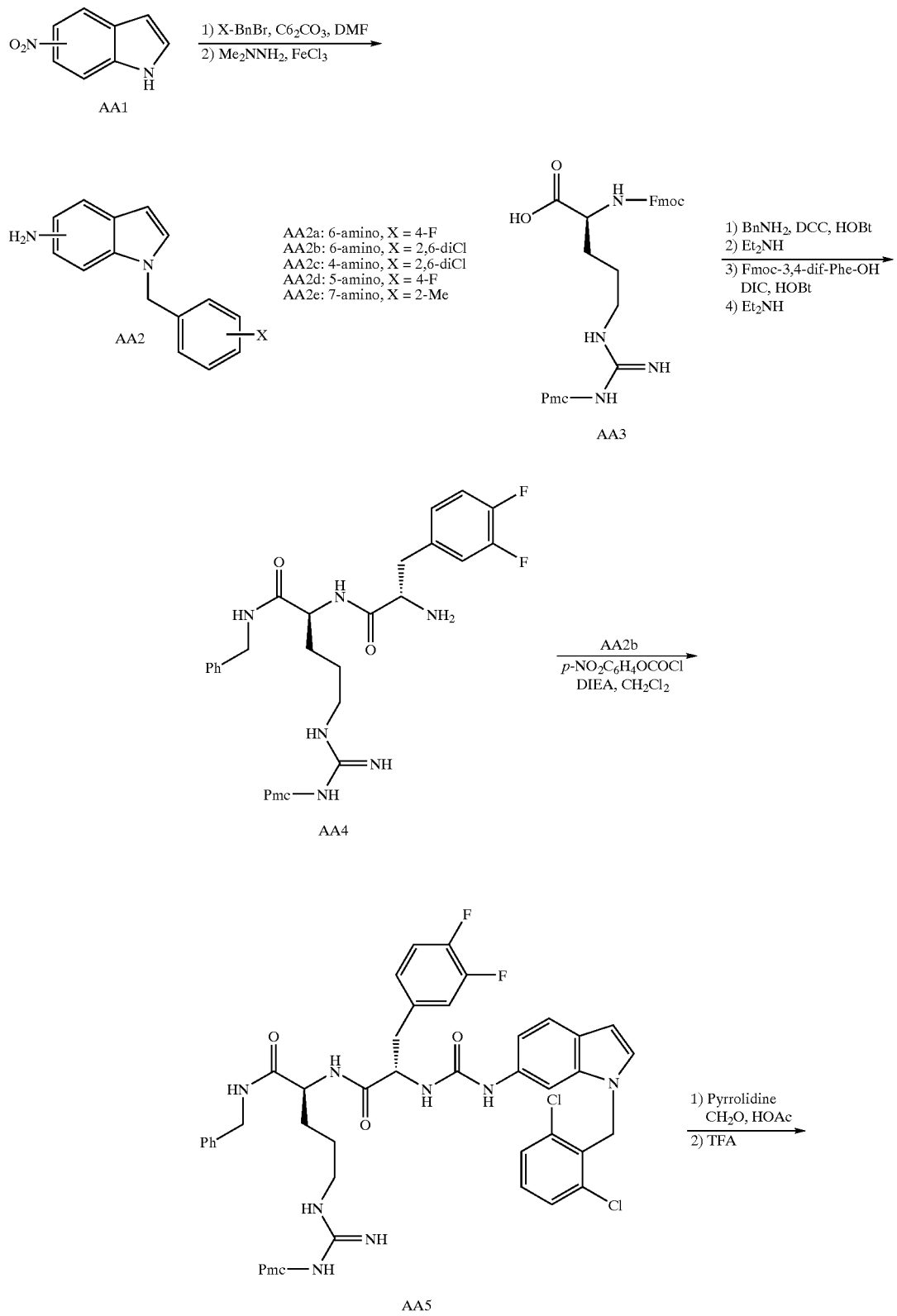
SCHEME AA

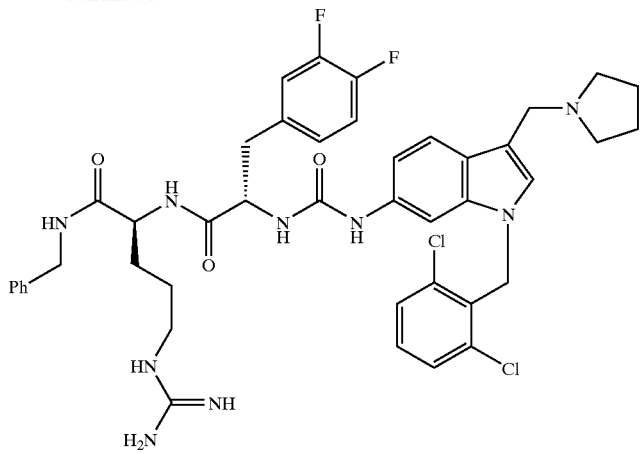

46

Scheme AB presents the solid-phase approach to producing the antagonist Compound 102. N-α-Fmoc-N-γ-Boc-2,4-diaminobutyric acid was coupled with benzyl amine in the presence of DCC and HOBt. The resulting benzylamide was treated with TFA in DCM to give AB2, which was then loaded onto 2-Cl-trityl-Cl resin in the presence of DIEA to afford AB3. Deprotection of the Fmoc group in AB3 with piperidine was followed by coupling with Fmoc-3,4-diF-Phe-OH in the presence of HBTU and HOBt. The resulting coupled product was deprotected again with piperidine to afford the resin-bound dipeptide AB4. Urea formation between AB4 and amino-indole AA2b was accomplished by using 4-nitrophenylchloroformate to provide AB5. Mannich reaction of AB5 with pyrrolidine and formaldehyde followed by resin cleavage with TFA afforded the crude product Compound 102 with >95% purity, which was further purified by reverse-phase HPLC.

SCHEME AB

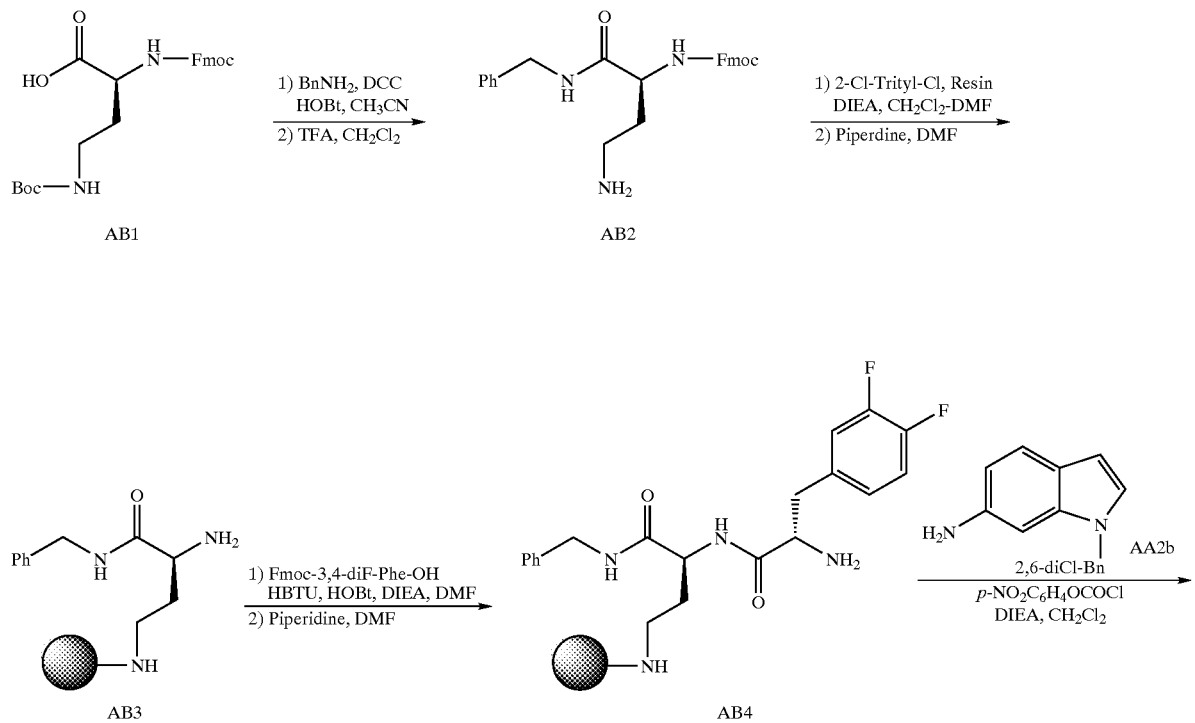

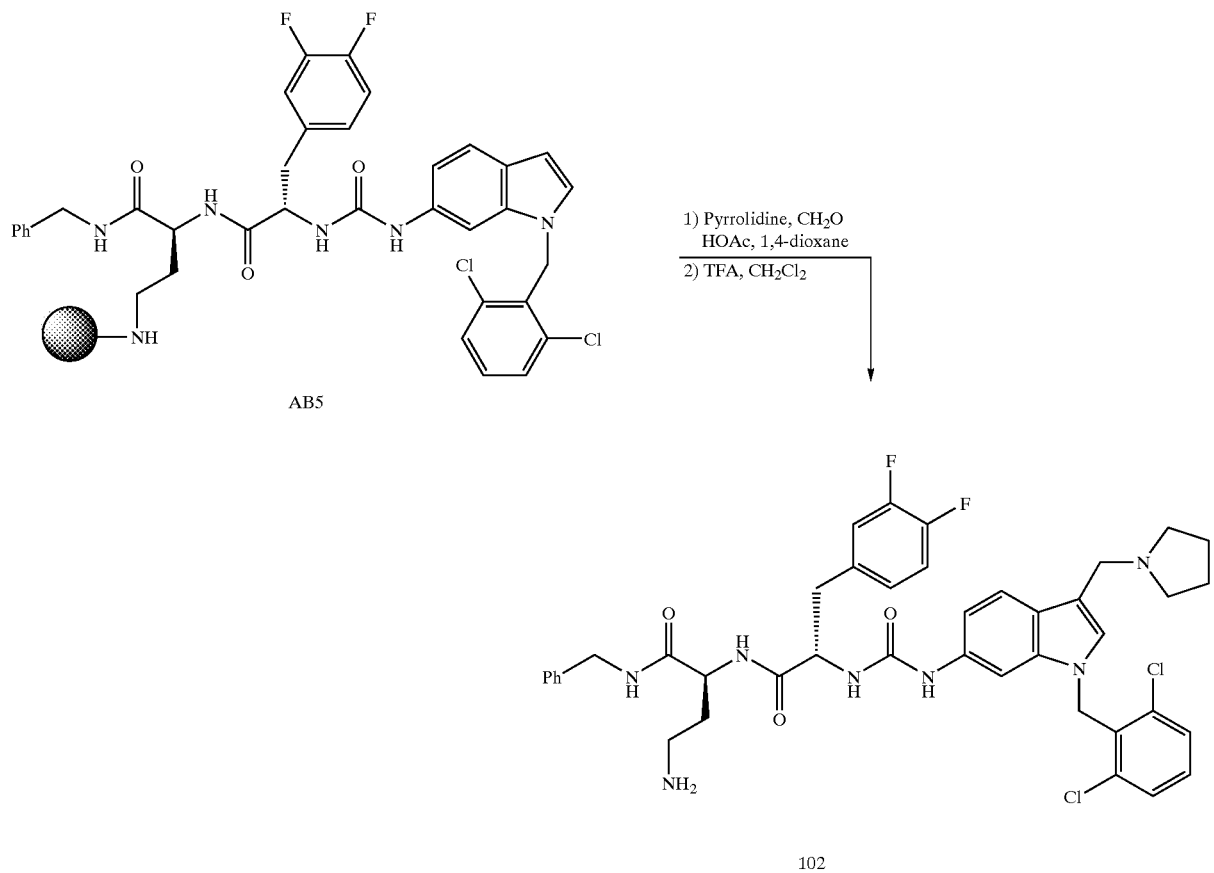
Similarly, Scheme AC represents another efficient solid-phase approach to the antagonists having an amine group at carboxy-terminus of the $A_2$.
Antagonists having an acetamidine group (e.g., Compounds 95, 118 and 139, as in Table 1) may be prepared by treating the corresponding amine with S-2-naphthylmethyl thioacetimidate hydrobromide.
SCHEME AC
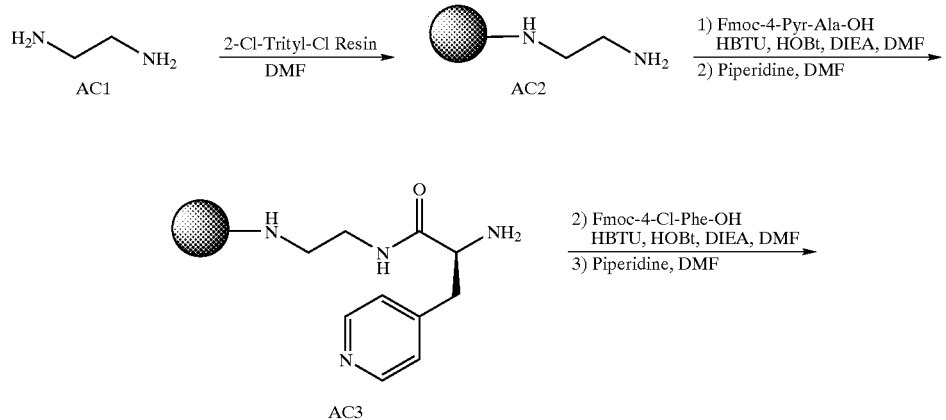

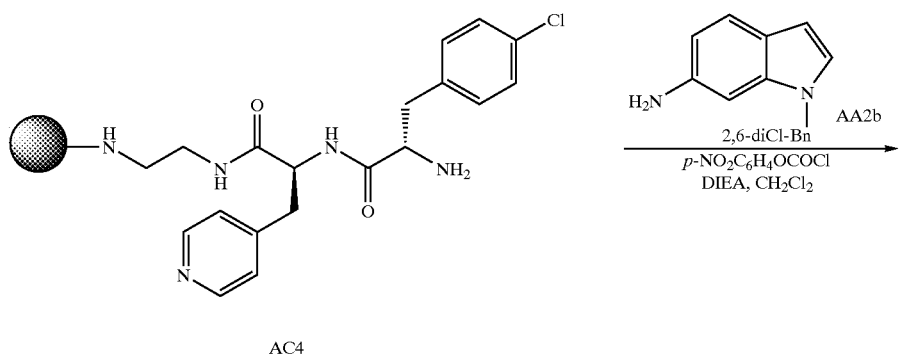

AC4

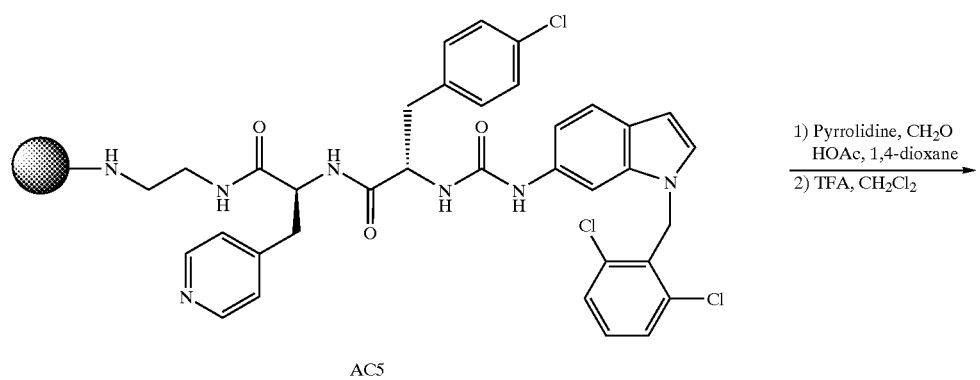

AC5

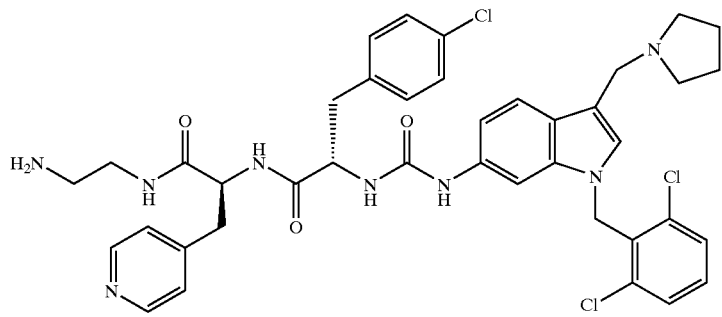

135

Scheme AD presents the preparation of 2-substituted 6-ureidoindoles (as in Table 5) by the synthesis of antagonist Compound 171. Palladium-mediated heteroannulation of terminal alkynes can be used as a key step for the preparation of 2-substituted indole intermediates. For example, to prepare the 2-phenyl-6-ureidoindole Compound 171, commercially available AD1 was converted to methanesulfonamide AD2 and subjected to palladium-mediated heteroannulation with phenylacetylene to give 2-phenylindole AD3. Deprotection of methylsulfonyl group in AD3 with KOH/MeOH afforded AD4. N-Alkylation of AD4 with 4-F-Bn-Br was followed by nitro reduction using $Me_2NNH_2/FeCl_3$ to afford intermediate AD5. Amino-indole AD5 was coupled with dipeptide AD6 (prepared as described in Scheme AAGeneric) in the presence of 4-nitrophenylchloroformate to give an urea, which was subjected to Mannich reaction followed by TFA cleavage to provide target 171.

By using the same method, 2-aryl, heteroaryl, alkyl, cycloalkyl, alkenyl, aralkyl-6-ureidoindoles can be prepared from the appropriate terminal alkynes.

To prepare the 2halo-6-ureidoindoles (e.g., Compounds 172 and 173), AD2 was subjected to palladium-mediated heteroannulation with (trimethylsilyl)acetylene. The resulting 2-(trimethylsilyl)indole was converted to 2-haloindoles by treating with N-chlorosuccinimide, N-bromosuccinimide, or N-iodosuccinimide. The 2-haloindole intermediates can then be converted to the targets using the method described in Scheme AD.

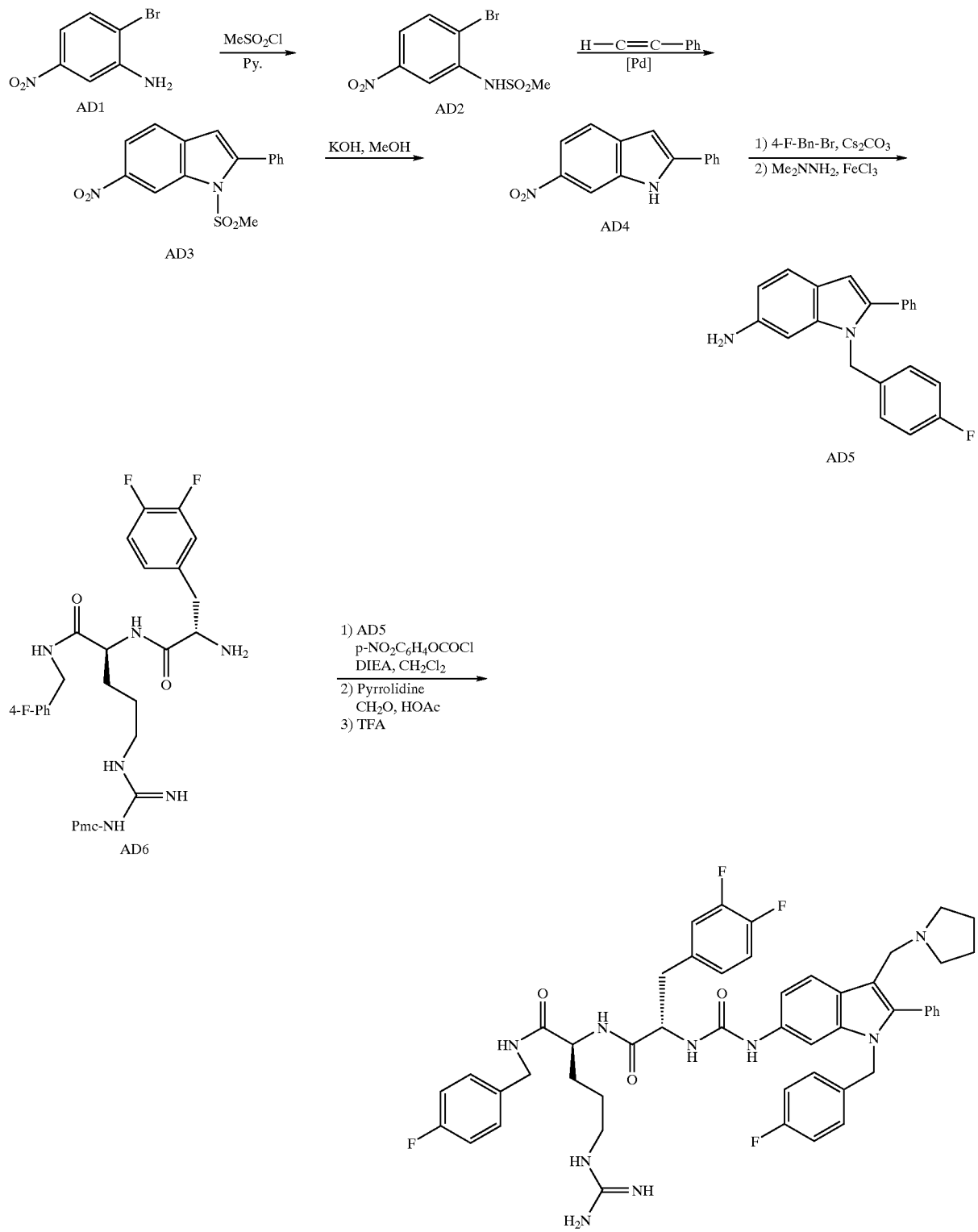
Scheme AE presents the synthesis of 6-amidoindoles (as in Table 6). Commercially available AE1 was converted to intermediate AE2 via alkylation followed by Mannich reaction and hydrolysis of methyl ester. The acid AE2 was then converted to the targets by coupling with a resin-bound dipeptide amine (e.g., AE3, prepared using the method as described for AC4 in Scheme AC) followed by resin cleavage with TFA. The coupling reaction may also be done in solution phase.

Extending the carbon chain from n being 1 to n being 2 at the 3-position of the indole [see general formula (I)] may be achieved by treating the dimethylamino Mannich base (when n is 1, $R_1$ is $NMe_2$) with KCN followed by reducing the cyano group to an amine.

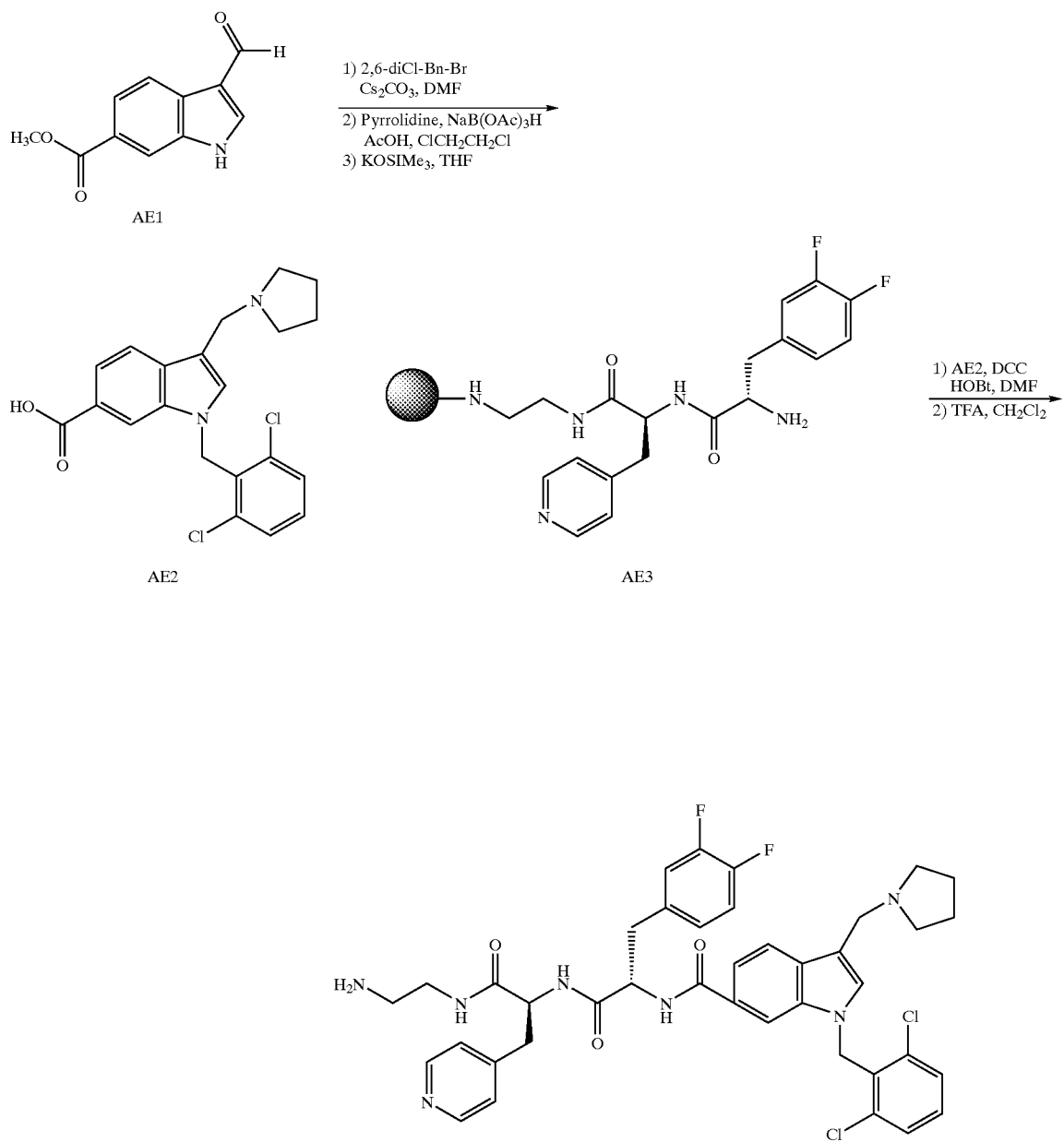

The thioureidoindoles [when X is S, as in general formula (I)] may be prepared as described hereinafter. Aminoindole substrate is reacted with thiocarbonyldiimidazole in a chlorinated solvent and then the imidazole by-product filtered from the solution. The solution then can be concentrated to afford the N-imidazolyl-N'-aminoindolyl-thiourea. This intermediate is then reacted with resin-bound peptide amine in a polar, aprotic solvent with heating (from about 80 to about 100° C.) to afford the resin-bound N-peptido-N'-aminoindolyl-thiourea product. The product is then liberated from the resin and purified as previously mentioned.

The utility of the compounds to treat PAR-1 mediated disorders (e.g., thrombotic disorders) can be determined according to the procedures described herein. The present invention therefore provides a method of treating PAR-1 mediated disorders (e.g., thrombotic disorders) in a subject in need thereof which comprises administering any of the compounds as defined herein in a quantity effective to treat PAR-1 mediated disorders. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.03 mg/kg to 100 mg/kg (preferred from about 0.1 mg/kg to about 30 mg/kg) of a compound of the present invention and may be given at a dosage of from about 0.1 mg/kg/day to about 300 mg/kg/day (preferred from about 1 mg/kg/day to about 50 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insulation. Alternatively, the composition may be presented in a form suitable for once-weekly or once-monthly administration; for example, an insoluble salt of the active compound, such as the decanoate salt may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The method of treating PAR-1 mediated disorders described in the present invention may also be carried out using a pharmaceutical composition comprising any of the compounds as defined herein and a pharmaceutically acceptable carrier. The pharmaceutical composition may contain between about 0.01 mg to about 100 mg, preferably from about 5 mg to about 50 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacryl-amidephenol, polyhydroxyethylaspartamidephenol or polyethyleneoxidepoly-lysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of PAR-1 mediated disorders is required.

The daily dosage of the products may be varied over a wide range from about 0.01 mg to about 1,000 mg per adult human per day. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day. Preferably, the range is from about 0.03 mg/kg to about 10 mg/kg of body weight per day. The compounds may be administered on a regimen of about 1 time per day to about 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

Biology

The compounds of the present invention are thrombin receptor (PAR-1) antagonists. The compounds interrupt platelet activation induced by thrombin's proteolytic cleavage of its platelet surface receptor, and thereby inhibit platelet aggregation. Such compounds are, therefore, useful in treating platelet-mediated thrombotic disorders (e.g., arterial and venous thrombosis, acute myocardial infarction, reocclusion following thrombolytic therapy and angioplasty, and a variety of vaso-occlusive disorders) and other PAR-1 mediated disorders.

In Vitro Thrombin Receptor Binding Assay CHRF membranes (Jones, Biochim. Biophys. Acta 1992, 1136, 272) are thawed from −70° C., centrifuged at maximum speed for 5 min, washed twice with binding buffer (50 mM HEPES containing 5 mM $MgCl_2$ and 0.1% BSA), and re-suspended in binding buffer (25 μg/100 mL). 100 μL of membranes are added to the 24-Wallac plates and delivered to the Tomtech apparatus. In a typical experiment, 6 μL of samples (from a 125 μg/mL intermediary plate, 20% DMSO) and 44 μL buffer are delivered to the plates (final conc. of compounds is 3.7 μg/mL, 0.6% DMSO). Similarly, 6 μL 20% DMSO and 44 μL buffer are delivered to both column 1 (NSB) and column 12 (TB). 10 μL Ser-pFPhe-Har-Leu-Har-Lys-Tyr-$NH_2$ (721–40; 500 μM in deionized water) is added to column 1. 50 μL tritiated 721–40 (specific activity 46 Ci/mmol) is added to all the wells. The plates are mixed well for 20 seconds, incubated for 30 min, and then harvested with 10 mM HEPES/138 mM NaCl using the Skatron harvester. The filters (GF/C Brandel FPXLR 296) are pre-soaked 3 h in 0.5% polyethylenimine in HEPES/0.1M N-acetylglucosamine) are set in saran wrap and dried for 3 min in the microwave, and placed in sample bags (Wallac 1450–432). 4.5 mL scintillation fluid (Wallac, Betaplate Scint 1205–440) is added. The bags are sealed, placed in filter cassettes (Wallac 1450–104), and analyzed on the microbeta counter.

In Vitro Inhibition of Thrombin-Induced Gel-Filtered Platelet Aggregation Assay

The percentage of platelet aggregation is calculated as an increase in light transmission of compound-treated platelet concentrate vs. control-treated platelet concentrate. Human blood is obtained from drug free, normal donors in tubes containing 0.13M sodium citrate. Platelet rich plasma (PRP) is collected by centrifugation of whole blood at 200×g for 10 min at 25° C. The PRP (5 mL) is gel filtered through Sepharose 2B (bed volume 50 mL), and the platelet count is adjusted to $2\times10^7$ platelets per sample. The following constituents are added to a siliconized cuvette: concentrated platelet filtrate and Tyrode's buffer (0.14M NaCl, 0.0027M KCl, 0.012M $NaHCO_3$, 0.76 mM $Na_2HPO_4$, 0.0055M glucose, 2 mg/mL BSA and 5.0 mM HEPES @ pH 7.4) in an amount equal to 350 μL 50 μL of 20 mM calcium and 50 μL of the test compound. Aggregation is monitored in a BIODATA aggregometer for the 3 min following the addition of agonist (thrombin 50 μL of 1 unit/mL).

Table 7 shows the biological activity of the compounds of the present invention. Table 7 contains $IC_{50}$ values (μM) of the compounds in a thrombin receptor binding assay, and $IC_{50}$ values (μM) against platelet aggregation stimulated by thrombin.

TABLE 7

| Cpd No. | Thrmb $IC_{50}{}^a$ | Bndg $IC_{50}{}^b$ |
|---|---|---|
| 1 | 0.83 | 0.6 |
| 2 | 7.8 | 33.6 |
| 3 | 21.4 | 10.7 |
| 4 | 14.7 | 1.3 |
| 5 | 2.9 | 1.8 |
| 6 | 3.5 | 6.6 |
| 7 | 1.31 | 3.6 |
| 8 | 8.0 | 2.3 |
| 9 | 2.5 | 10.4 |
| 10 | >10 | 4.8 |
| 11 | 19.9 | 2.5 |
| 12 | 43.2 | 15.9 |
| 13 | 16.2 | 4.5 |
| 14 | 0.49 | 1.4 |
| 15 | 11.8 | 4.3 |
| 16 | 25.8 | 11.5 |
| 17 | 0.42 | 0.97 |
| 18 | 14 | 3.7 |
| 19 | 3.2 | 1.6 |
| 20 | 26.6 | 17.1 |
| 21 | 3.2 | 1.1 |
| 22 | 3.0 | 4.0 |
| 23 | 8.6 | 3.1 |
| 24 | 34.8 | 4.8 |
| 25 | 37.1 | — |
| 26 | 0.55 | 4.3 |
| 27 | 27.3 | 14.6 |
| 28 | 13.8 | 4.1 |
| 29 | >10 | 8.4 |
| 30 | >10 | 9.0 |
| 31 | >10 | 8.4 |
| 32 | 48.6 | 7.3 |
| 33 | 54.7 | 5.4 |
| 34 | 16.3 | 9.7 |
| 35 | 13.0 | 13.1 |
| 36 | 6.8 | 16.7 |
| 37 | 4.4 | 20.3 |
| 38 | 2.5 | 33.5 |
| 39 | 3.5 | 21.5 |
| 40 | >10 | 3.9 |
| 41 | 4.8 | 10.4 |
| 42 | 24.7 | 2.0 |
| 43 | 33.5 | 5.0 |
| 44 | 9.7 | 3.3 |
| 45 | >10 | 13.9 |
| 46 | 0.28 | 0.47 |
| 47 | 0.88 | 1.2 |
| 48 | 0.50 | 7.6 |
| 49 | 6.1 | 1.0 |
| 50 | 0.80 | 7.6 |
| 51 | 0.68 | 0.8 |
| 52 | 0.48 | 5.3 |
| 53 | 1.0 | 8.8 |
| 54 | 0.50 | 16 |
| 55 | 0.34 | 11.3 |
| 56 | 3.8 | 11.4 |
| 57 | 1.8 | 0.30 |
| 58 | >10 | 1.5 |
| 59 | 0.88 | 0.14 |
| 60 | 0.93 | 2.8 |
| 61 | 1.4 | 0.3 |
| 62 | 1.26 | 0.03 |
| 63 | 0.70 | 0.13 |
| 64 | 2.2 | 0.23 |
| 65 | 1.0 | 0.22 |
| 66 | 0.24 | 1.1 |
| 67 | 0.42 | 0.45 |
| 68 | 4.7 | 6.5 |
| 69 | 0.31 | 0.62 |
| 70 | 0.31 | 0.32 |
| 71 | 0.55 | 3.0 |
| 72 | 0.46 | 1.3 |
| 73 | 2.4 | 7.5 |
| 74 | 2.9 | 0.56 |
| 75 | 2.2 | 0.23 |
| 76 | 1.1 | 0.20 |
| 77 | 29.5 | 0.62 |
| 78 | 1.3 | 1.5 |
| 79 | 1.3 | 0.17 |
| 80 | 11.3 | 5.9 |
| 81 | 0.41 | 0.07 |
| 82 | 1.5 | 0.31 |
| 83 | 0.43 | 0.68 |
| 84 | 14.9 | 3.2 |
| 85 | 4.8 | 1.6 |
| 86 | 2.9 | 0.51 |
| 87 | 1.3 | 0.28 |
| 88 | 12.6 | 1.7 |
| 89 | 33.8 | 3.7 |
| 90 | >10 | 15.8 |
| 91 | 22.4 | 4.0 |
| 92 | 1.3 | 1.0 |
| 93 | 0.74 | 0.50 |
| 94 | 10.0 | 0.81 |
| 95 | 0.41 | 0.37 |
| 96 | 1.0 | 2.8 |
| 97 | 18.8 | 1.7 |
| 98 | 1.8 | 2.3 |
| 99 | 0.74 | 1.4 |
| 100 | 0.60 | 1.3 |
| 101 | 0.41 | 0.92 |
| 102 | 0.16 | 0.50 |
| 103 | 0.54 | 1.2 |
| 104 | 0.53 | 11.2 |
| 105 | 0.64 | 7.5 |
| 106 | 1.1 | 3.3 |
| 107 | 1.8 | 8.0 |
| 108 | 3.7 | 2.6 |
| 109 | 0.84 | 0.61 |
| 110 | 3.7 | 2.9 |
| 111 | 3.2 | 1.9 |
| 112 | 0.93 | 2.0 |
| 113 | 0.72 | 0.85 |
| 114 | 2.4 | 0.26 |
| 115 | 2.7 | 0.37 |
| 116 | 1.1 | 0.41 |
| 117 | 4.1 | 1.0 |
| 118 | 0.28 | 0.43 |
| 119 | 3.2 | 6.2 |
| 120 | >10 | 18.1 |
| 121 | 10.4 | 12.2 |
| 122 | 3.5 | 10.5 |
| 123 | 14.8 | 4.4 |
| 124 | 0.44 | 1.2 |
| 125 | 0.43 | 0.66 |
| 126 | 0.46 | 1.5 |
| 127 | 0.93 | 2.4 |
| 128 | 18.8 | 3.4 |

TABLE 7-continued

| Cpd No. | Thrmb IC$_{50}$[a] | Bndg IC$_{50}$[b] |
|---|---|---|
| 129 | 0.86 | 2.5 |
| 130 | 27.8 | 4.8 |
| 131 | 0.94 | 1.9 |
| 132 | 22.0 | 4.2 |
| 133 | 0.86 | 1.5 |
| 134 | 0.95 | 1.2 |
| 135 | 0.69 | 0.89 |
| 136 | 0.55 | 1.1 |
| 137 | 0.94 | 0.81 |
| 138 | 0.33 | 2.0 |
| 139 | 0.33 | 1.0 |
| 140 | 0.74 | 0.12 |
| 141 | 0.2 | 0.07 |
| 142 | 1.9 | 0.48 |
| 143 | 0.29 | 0.02 |
| 144 | 0.32 | 0.07 |
| 145 | 0.25 | 0.50 |
| 146 | 11.1 | 2.8 |
| 147 | 4.4 | 0.42 |
| 148 | 1.4 | 0.14 |
| 149 | 1.2 | 0.15 |
| 150 | 1.4 | 0.10 |
| 151 | 2.9 | 0.45 |
| 152 | 40.7 | 9.9 |
| 153 | 0.79 | 27 |
| 154 | 12.9 | 0.75 |
| 155 | 11.0 | 13.5 |
| 156 | 0.60 | 0.04 |
| 157 | 0.66 | 0.48 |
| 158 | 0.74 | 1.8 |
| 159 | 0.43 | 0.70 |
| 160 | 0.60 | — |
| 161 | 0.52 | — |
| 162 | 13.0 | 5.3 |
| 163 | 30.0 | 3.0 |
| 164 | 13.6 | 11.8 |
| 165 | 4.8 | 49.6 |
| 166 | 40.3 | 2.0 |
| 167 | 8.5 | 67.6 |
| 168 | 8.3 | 64.3 |
| 169 | 12.8 | 8.8 |
| 170 | 23.3 | 21.6 |
| 171 | 1.0 | 0.10 |
| 172 | >10 | 6.8 |
| 173 | 2.0 | 0.76 |
| 174 | 71.5 | — |
| 175 | 1.6 | 0.09 |
| 176 | 45.7 | 43.2 |
| 177 | 4.4 | 0.62 |
| 178 | 40.7 | 9.9 |

[a]Thrombin-induced aggregation of gel-filtered platelets in μM.
[b]Thrombin receptor binding in μM.

EXAMPLES

General Procedures. Resins and protected amino acids were purchased from Novabiochem, Bachem Bioscience, Advanced ChemTech or Synthe Tech. All other chemicals were obtained from commercial suppliers and used without further purification. $^1$H and $^{13}$C NMR spectra were recorded on a Bruker AC 300B (300 MHz proton) or a Bruker AM-400 (400 MHz proton) spectrometer with Me$_4$Si as an internal standard (s=singlet, d=doublet, t=triplet, br=broad). APCI-MS and ES-MS were recorded on a VG Platform II mass spectrometer; methane was used for chemical ionization, unless noted otherwise. Accurate mass measurements were obtained by using a VG ZAB 2-SE spectrometer in the FAB mode. TLC was performed with Whatman 250-μm silica gel plates. Preparative TLC was performed with Analtech 1000-μm silica gel GF plates. Flash column chromatography was conducted with flash column silica gel (40–63 μm) and column chromatography was conducted with standard silica gel. HPLC separations were carried out on three Waters PrepPak® Cartridges (25×100 mm, Bondapak® C18, 15–20 μm, 125 Å) connected in series; detection was at 254 nm on a Waters 486 UV detector. Analytical HPLC was carried out on a Supelcosil ABZ+PLUS column (5 cm×2.1 mm), with detection at 254 nm on a Hewlett Packard 1100 UV detector. Microanalysis was performed by Robertson Microlit Laboratories, Inc.

In the examples and throughout this application, the following abbreviations have the meanings recited hereinafter

| | |
|---|---|
| Ac | Acetyl |
| ACN | Acetonitrile |
| Bn | Benzyl |
| Boc | t-Butoxycarbonyl |
| DCC | 1,3-Dicyclohexylcarbodiimide |
| DCM | Dichloromethane |
| DEA | Diethylamine |
| DIC | Diisopropylcarbodiimide |
| DIEA | Diisopropylethylamine |
| DMAP | 4-Dimethylaminopyridine |
| DMF | N,N-Dimethylformamide |
| Et | Ethyl |
| Fmoc | 9-Fluorenylmethoxycarbonyl |
| h | Hour |
| HBTU | 2-(1H-Benzotriazole-1-yl)-1,1,3,3-tetramethyluronium hexafluorophosphate |
| HOAc | Acetic acid |
| HOBT | Hydroxybenzotriazole |
| i-Pr or iPr | Isopropyl |
| Me | Methyl |
| min | Minute |
| Pmc | 2,2,5,7,8-Pentamethylchroman-6-sulfonyl |
| Py | Pyridine |
| rt | room temperature |
| THF | Tetrahydrofuran |
| TFA | Trifluoroacetic acid |
| Tr | Triphenylmethyl |

Example 1

Convergent solution-phase synthesis of Compound 46 (Scheme AA)

L-Argininamide,3,4-difluoro-N-[[[1-[(2,6-dichlorophenyl)methyl]-3-(1-pyrrolidinylmethyl)-1H-indol-6-yl]amino]carbonyl]-L-phenylalanyl-N-(phenylmethyl)-(Compound 46)

6-Nitro ndole AA1 (8.0 g, 49.2 mmol) was dissolved in dry DMF (60 mL) under argon, cesium carbonate (16.0 g, 49.2 mmol) was added and the mixture was stirred at about 45° C. for about 30 min. After cooling to about rt, the mixture was stirred while 2,6-dichlorobenzyl bromide (13.0 g, 54 mmol) in DMF (40 mL) was added over about 1 h; then the reaction was stirred at about rt for about 16 h. The solution was then added portionwise to water (1.6 L) with vigorous stirring, which precipitated a solid, stirring was continued for about 3 h. A yellow solid was filtered and washed with hexane (3×), then air dried. The resulting solid was combined in MeOH (150 mL) with charcoal (1.1 g, 92 mmol) and ferric chloride hexahydrate (0.54 g. 2.0 mmol), 1,1 dimethylhydrazine (27.2 g, 440 mmol) was then added and the reaction was refluxed for about 16 h. After cooling to about rt, the reaction was filtered through dicalite and the filtrate was evaporated in vacuo to a yellow solid. The solid was partitioned between 1N HCl (750 mL) and diethyl ether (750 mL); the solid was combined with the aqueous acid solution, the pH was brought to greater than pH 13 with 3N NaOH and the solution then extracted with DCM (2× 400 mL). The DCM solution was washed with saturated NaHCO$_3$ (2×), brine, dried (K$_2$CO$_3$) and evaporated in vacuo to a solid, which was triturated with hexane (3×) to afford a light tan solid AA2b.

Fmoc-arginine(PMC)—OH AA3 (3.83 g, 5.0 mmol) and HOBT (0.76 g, 5.0 mmol) were combined in acetonitrile (100 mL) and benzylamine (0.54 g, 5.0 mmol) was added dropwise at about rt, followed by DCC (2.06 g, 10.0 mmol) and stirred for about 16 h. A solid was filtered and the filtrate was evaporated in vacuo to an oil, which was then dissolved in ethyl acetate (100 mL) and washed with saturated NaHCO$_3$ (2×), brine (2×), then dried (Na$_2$SO$_4$) and evaporated in vacuo to a solid, which was triturated with hexane (2×) to give a solid (impure with dicyclohexylurea). A portion of this solid (1.17 g, 1.25 mmol) was dissolved in acetonitrile (30 mL), diethyl amine (1.5 mL) was added and the reaction was stirred at about rt for about 1 h. The solution was then evaporated in vacuo to a solid, which was triturated with hexane (2×). The solution was then evaporated in vacuo to a solid, which was then combined in ACN (25 mL) with Fmoc-3,4difluorophenylalanine (0.53 g, 1.25 mmol) and HOBT (0.19 g, 1.25 mmol). DIC (0.32 g, 2.5 mmol) was added and the reaction was stirred at about rt for about 16 h. Fmoc-protected dipeptide was filtered (0.77 g) and stirred in ACN (30 mL) with diethyl amine (1.5 mL) for about 2.5 h. The reaction was evaporated in vacuo to an oil, which was triturated with hexane (3×) to the white solid AA4.

Aminoindole AA2b (142 mg, 0.49 mmol) and DIEA (63 mg, 0.49 mmol) in DCM (3 mL) was added to 4-nitrophenylchloroformate (99 mg, 0.49 mmol) in dry DCM (120 mL) at about −20° C. and stirred at about −20° C. for about 30 min; the dipeptide AA4 (380 mg, 0.49 mmol) and DIEA (63 mg, 0.49 mmol) in DCM (3 mL) was then added in, stirred at about −20° C. for about 30 min and then at about rt for about 16 h. Solid urea AA5 had precipitated out, was then filtered and let air dry. Pyrrolidine (90 mg, 1.25 mmol) was added to glacial acetic acid (5.0 mL) under argon, formaldehyde (37%, 0.10 g, 1.25 mmol) was added in and the reaction was stirred at about rt for about 25 min. Indole urea AA5 (0.43 g, 0.42 mmol) was added and the reaction stirred at about rt for about 2 h. The solution was evaporated in vacuo to an oil, which was partitioned between chloroform:2-propanol (10:1, 75 mL) and 1N NaOH (30 mL). The organic layer was washed with saturated NaHCO$_3$ (2×), brine (2×) and then dried (K$_2$CO$_3$) and evaporated in vacuo to a tan solid. The solid product was stirred with TFA:DCM:anisole (50:50:1; 40 mL) at about rt for about 3 h and then evaporated in vacuo to an oil, which was triturated with ethyl ether (3×) to give the crude product Compound 46 as an off white solid. Purification was accomplished via reverse-phase HPLC using 0.16% TFA in acetonitrile:0.20% TFA in water (33:67) and upon lyophilization afforded a white floccular solid. The solid was dissolved in 1N HCl:ACN (1:1, 50 mL), then frozen and lyophilized to a solid; the procedure was repeated for two more times to afford the floccular HCl salt of product Compound 46. $^1$H NMR (DMSO/D$_2$O) δ 7.80 (s, 1H), 7.65–7.00 (m, 14H), 5.45 (s, 2H), 4.60 (m, 1H), 4.40–4.25 (m, 5H), 3.30 (m, 2H), 3.20–3.00 (m, 5H), 2.85 (dd, 1H), 2.05–1.40 (m, 8H). ES-MS m/z 846 (MH$^+$). Anal. Calcd. for C$_{43}$H$_{47}$Cl$_2$F$_2$N$_9$O$_3$.2.0HCl.1.50H$_2$O (846.81/946.75): C, 54.55; H, 5.54: N, 13.32; Cl, 14.98; H$_2$O, 2.85. Found: C, 54.44; H, 5.47; N. 13.43; Cl, 14.85; H$_2$O, 3.01.

Example 2

Solid-phase synthesis of Compound 102
(Scheme AB)

Benzenepropanamide, N-[(1S)-3-amino-1-[[(phenylmethyl)amino]carbonyl]propyl]-α-[[[[1-[(2,6-dichlorophenyl)methyl]-3-(1-pyrrolidinylmethyl)-1H-indol-6-yl]amino]carbonyl]amino]-3,4difluoro-, (βS)-(Compound 102)

To a solution of N-α-Fmoc-N-γ-Boc-diaminobutyric acid (4.0 g, 9.1 mmol) and BnNH$_2$ (1.07 g, 10 mmol) in CH$_3$CN (150 mL), HOBt (1.85 g, 13.7 mmol) and DCC (2.82 g, 13.7 mmol) were added. The mixture was stirred at about rt for about 2.5 h, at which time TLC indicated that reaction was complete. The resulting white precipitates (a mixture of the desired product and dicyclohexylurea) were collected by filtering and washing with CH$_3$CN. The combined filtrates were concentrated under vacuo and the residue was dissolved in EtOAc (150 mL). The solution was washed with saturated NaHCO$_3$, H$_2$O and brine, then dried (Na$_2$SO$_4$) and evaporated to give a white powder which was recrystallized from CH$_3$CN to afford an additional product. The combined crude products were treated with 50% TFA in CH$_2$Cl$_2$ (80 mL) at about rt for about 1 h. The volatiles were removed under vacuo, and the residue was triturated with Et$_2$O to give AB2 as a colorless solid. $^1$H NMR showed the product was a mixture of AB2 and dicyclohexylurea (ratio 1:1.4). To a solution of the crude AB2 (6.16 g, 7.14 mmol) and DIEA (2.71 g, 21.0 mmol) in DCM-DMF (1:1, 120 mL), 2-chlorotrityl chloride resin (4.0 g, 4.2 mmol) was added; the suspension was stirred at about rt for about 20 h. The reaction mixture was filtered on a sintered glass funnel and washed with DMF (2×), MeOH (3×) and DCM (3×), then dried in vacuo to give the resin. A portion of the resin (4.9 g) was treated with 20% piperidine in DMF (80 mL) at about rt for about 2 h, then filtered and washed with DMF (2×), MeOH (2×), DCM (2×) and Et$_2$O (2×) and dried in vacuo to afford resin AB3 (loading level by of 0.81 mmol/g, based on the mass loss during removing Fmoc group). A portion of AB3 (1.6 g, 1.3 mmol) was suspended in DMF (50 mL) and treated with Fmoc-3,4-diF-Phe-OH (1.65 g, 3.9 mmol), HOBT (0.53 g, 3.9 mmol), DIEA (1.01 g, 7.8 mmol) and HBTU (1.48 g, 3.9 mmol). The suspension was stirred at about rt for about 20 h, then filtered and washed with DMF, MeOH and DCM. The resulting resin was treated with 20% piperidine in DMF (40 mL) at about rt for about 2 h, then filtered and washed with DMF (2×), MeOH (2×), DCM (2×) and Et$_2$O (2×) to afford resin AB4. To 4-Nitrophenyl chloroformate (613 mg, 3.0 mmol) in dry DCM (60 mL) at about −20° C., a solution of AA2b (1.14 g, 3.9 mmol) and DIEA (1.0 g, 8.0 mmol) in DCM (20 mL) was added over about 4 min and then stirred at about −20° C. for about 20 min. The dipeptidyl resin AB4 (1.14 g, 0.80 mmol) was added and stirred at about −20° C. for about 25 min and then at about rt for about 18 h. The suspension was filtered and washed with DMF, MeOH, DCM and Et$_2$O and then dried in vacuo to give resin AB5. To a solution of pyrrolidine (2.33 g, 33.0 mmol) and formaldehyde (37%, 2.14 g, 26.4 mmol) in 1,4-dioxane/glacial acetic acid (4:1; 60 mL) was added resin AB5 (1.20 g, 0.66 mmol) in one portion. The suspension was stirred at about rt for about 16 h, then filtered and washed with MeOH, DCM and Et$_2$O and dried in vacuo to afford resin. A portion of the resin (400 mg, 0.23 mmol) was treated with TFA:DCM:anisole (30:70:0.50, 12 mL) at about rt for about 1.5 h; the reaction mixture was then filtered and washed with fresh 30% TFA in DCM. The filtrates were combined and evaporated in vacuo and the residue triturated with diethyl ether (3x) to give the crude product as a light purple solid (>95% purity by HPLC). The crude product was purified by reverse-phase HPLC to give Compound 102 as a colorless solid. $^1$H NMR (CD$_3$OD) δ 7.83 (s, 1H), 7.62–7.02 (m, 14H), 5.43 (d, J=2.7 Hz, 2H), 4.53–4.46 (m, 2H), 4.44 (s, 2H), 4.38 (d, J=5.6 Hz, 2H), 3.42–3.31 (m, 2H), 3.29–2.93 (m, 6H), 2.22–1.85 (m, 6H). ES-MS m/z 790 (MH$^+$). Anal. calcd. for C$_{41}$H$_{43}$Cl$_2$F$_2$N$_7$O$_3$.2.74CF$_3$CO$_2$H.0.50H$_2$O (790.74/1112.18): C, 50.20; H, 4.24; N, 8.82; F, 17.46. Found: C, 50.17; H, 4.10; N, 8.79; F, 17.73.

Example 3

Solid-phase synthesis of Compound 135 (Scheme AC)

L-Alaninamide, 4-chloro-N-[[[1-[(2,6-dichlorophenyl)methyl]-3-(1-pyrrolidinylmethyl)-1H-indol-6-yl]amino]carbonyl]-L-phenylalanyl-N-(2-aminoethyl)-3-(4-pyridinyl)-(Compound 135)

2-Chlorotrityl chloride resin (4.8 g, 8.65 mmol; Advanced ChemTech) was stirred in DMF (100 mL) as ethylene diamine AC1 (15.6 g, 260 mmol) was added, the reaction was stirred at about rt for about 16 h. The resin AC2 was filtered on a sintered glass funnel and washed with DMF (4x), MeOH (3x) and DCM (3x), then dried in vacuo. A portion of resin AC2 (2.0 g, 3.5 mmol) was placed in a solid phase hour-glass reactor and agitated (nitrogen bubbling) in DMF (40 mL) with Fmoc-4-pyridyl alanine (3.9 g, 10 mmol), HOBT (1.53 g, 10 mmol) and DIC (1.26 g, 10 mmol) for about 16 h. The solution was drawn off and the resin was washed with DMF (4x), DCM (4x) and DMF (2x) and then combined with 20% piperidine in DMF (25 mL) and agitated for about 1.5 h. The solution was drained and the resin AC3 was washed with DMF (5x) then agitated in DMF (20 mL) with Fmoc-4-Chlorophenyl alanine (4.22 g, 10 mmol), HOBT (1.53 g, 10 mmol) and DIC (1.26 g, 10 mmol) at about rt for about 16 h. The solution was removed and the resin was washed with DMF (5x), MeOH (3x), DCM (3x) and DMF (2x), then combined with 20% piperidine in DMF (25 mL) and agitated for about 1 h. The solution was drained and the resin was washed with DMF (4x), DCM (4x) and dry DCM (3x) and stored in vacuo to give AC4. To 4-Nitrophenyl chloroformate (2.02 g, 10 mmol) in dry DCM (200 mL) at about −20° C., a solution of AA2b (3.6 g, 12.5 mmol) and DIEA (2.58 g, 20 mmol) in DCM (50 mL) was added over about 10 min and stirred at about −20° C. for about 20 min. The dipeptidyl resin (1.5 g, 2.5 mmol) was added and stirred at about −20° C. for about 25 min. and then at about rt for about 16 h. The resin AC5 was filtered and washed with DMF (3x), MeOH (3x) and DCM (4x), then dried in vacuo. Pyrrolidine (8.9 g. 125 mmol) was added to 1,4-dioxane:glacial acetic acid (4:1; 240 mL) and, at about rt, formaldehyde (37%, 8.11 g, 100 mmol) was added; the solution was then stirred under argon for about 15 min; the resin AC5 from above was added and stirred for about 16 h. The resin was filtered and washed with DMF (4x), MeOH (4x), DCM (2x) and MeOH (3x), then dried in vacuo at about rt for about 72 h. The dried resin was combined with TFA:DCM:anisole.(30:70:0.50, 50 mL) and stirred at about rt for about 1 h. The resin was filtered and washed with fresh 30% TFA in DCM; the filtrates were combined and evaporated in vacuo to an oil, which was triturated with diethyl ether (3x) to give the crude product Compound 135 as a white solid. Purification was accomplished via reverse-phase HPLC using 0.16% TFA in ACN:0.20% TFA in water (33:67) and upon lyophilization afforded a white floccular solid. The solid was dissolved in 1N HCl (25 mL) and evaporated in vacuo to a solid; this procedure was repeated twice. The solid was then dissolved in 1N HCl (25 mL), frozen and lyophilized to give Compound 135 as a white floccular solid. $^1$H NMR (CD$_3$OD) δ 8.55 (d, J=8.0, 2H), 7.82–7.05 (m, 13H), 5.58 (s, 2H), 4.70 (m, 1H), 4.45 (m, 3H), 3.55–2.90 (m, 12H), 2.20–1.90 (m, 4H). ES-MS m/z 789 (MH$^+$). Anal. calcd. for C$_{40}$H$_{43}$Cl$_3$N$_8$O$_3$.3.0HCl.4.75H$_2$O (790.19/985.22): C, 48.76; H, 5.68; N, 11.37; Cl, 21.60; H$_2$O, 8.68. Found: C, 48.41; H, 5.41; N, 11.37; Cl, 21.87; H$_2$O, 7.52.

Example 4

Synthesis of Compound 171 (Scheme AD)

L-Argininamide,3,4-difluoro-N-[[[1-[(4-fluorophenyl)methyl]-2-phenyl-3-(1-pyrrolidinylmethyl)-1H-indol-6-yl]amino]carbonyl]-L-phenylalanyl-N-[(4-fluorophenyl)methyl]-(Compound 171)

To a mixture of AD2 (207 mg, 0.7 mmol, prepared from 2-bromo-5-nitroaniline, Yamanaka, Chem. Pharm. Bull. 1988, 36, 1305), phenylacetylene (215 mg, 2.1 mmol) and copper (I) iodide (13 mg, 0.07 mmol) In Et$_3$N-DMF (3:2, 2.5 mL), bis(triphenylphosphine)palladium(II) chloride (25 mg, 0.035 mmol) was added. The reaction mixture was stirred at about 70° C. for about 16 h, then cooled to about rt, diluted with H$_2$O (15 mL) and extracted with Et$_2$O (30 mL X 2). The combined extracts were washed with brine, then dried (Na$_2$SO$_4$), evaporated and purified by silica gel chromatography (Hexane:EtOAc, gradient from 6:1 to 2:1) to give AD3 as a yellow solid and the corresponding de-sulfonyl product AD4 as a yellow solid. AD3 was treated with 4% KOH in MeOH (15 mL) at about rt for about 2 h and the solvent was then evaporated. The residue was partitioned between EtOAc (30 mL) and H$_2$O (10 mL); the organic layer was separated, washed with H$_2$O (5 mL) and brine (5 mL), then dried (Na$_2$SO$_4$) and evaporated in vacuo to give AD4 as a yellow solid. AD4 (65 mg, 0.27 mmol) was dissolved in dry DMF (4 mL) under argon, cesium carbonate (134 mg, 0.41 mmol) was added and the mixture was stirred at about 50° C. for about 20 min. After cooling to about rt, the mixture was stirred as 4-fluorobenzyl bromide (66 mg, 0.35 mmol) was added; then the reaction was stirred at about rt for about 2 h. To the reaction mixture were added H$_2$O (8 mL) and EtOAc (30 mL). The organic layer was separated, washed with H$_2$O (8 mL) and brine (8 mL), then dried (Na$_2$SO$_4$) and evaporated in vacuo. The resulting solid was dissolved in MeOH (5 mL) and the solution was treated with charcoal (24 mg, 2.0 mmol), ferric chloride hexahydrate (13.6 mg, 0.05 mmol) and 1,1 dimethylhydrazine (451 mg, 7.5 mmol). The mixture was stirred at about 75° C. for about 20 h and then filtered through Celite. The filtrate was evaporated in vacuo, and the residue was partitioned between Et$_2$O (40 mL) and H$_2$O (10 mL). The organic layer was separated, washed with brine (10 mL), then dried (Na$_2$SO$_4$) and evaporated in vacuo to give AD5 as a viscous yellow solid. ES-MS m/z 317 (MH$^+$). Aminoindole AD5 (60 mg, 0.19 mmol) and DIEA (25 mg, 0.19 mmol) in DCM (3 mL) were added to 4-nitrophenylchloroformate (38 mg, 0.19 mmol) in dry DCM (40 mL) at about −20° C. and stirred at about −20° C. for about 20 min; the dipeptide ADS (0.19 mmol) and DIEA (25 mg, 0.19 mmol) in DCM (2 mL) were added in, stirred at about −20° C. for about 30 min and then at about rt for about 16 h. A portion of the urea product had precipitated out and was filtered. The filtrate was evaporated in vacuo and the residue was triturated with hexane:DCM (5:1). The resulting solid was dissolved in EtOAc (30 mL), washed with H₂O (8 mL) and brine (8 mL), then dried (Na₂SO₄) and evaporated in vacuo to give an additional urea product. The urea product was treated with a solution of pyrrolidine (30 mg, 0.43 mmol) and formaldehyde (37%, 25 mg, 0.31 mmol) in glacial acetic acid (3 mL). The mixture was stirred at about rt for about 18 h and then concentrated in vacuo. The residue was dissolved in EtOAc (30 mL), washed with H₂O (5 mL) and brine (5 mL), then dried (Na₂SO₄) and evaporated in vacuo. The resulting solid was stirred with TFA:DCM:anisole (90:9:1; 5 mL) at about rt for about 3 h; the volatiles were then evaporated in vacuo and the residue triturated with ethyl ether to give a crude product which was purified by reverse-phase HPLC using 0.16% TFA in CH₃CN:0.20% TFA in water (gradient from 30:70 to 95:5 within about 40 min) to afford Compound 171 as a colorless solid. ¹H NMR (CD₃OD) δ 7.72–6.80 (m, 19H). 5.21 (s, 2H), 4.50–4.32 (m, 6H), 3.40–2.88 (m, 8H), 1.95–1.50 (m, 8H). ES-MS m/z 890 (MH⁺).

Example 5

Synthesis of compound 175 (Scheme AE)

L-Alaninamide, N-[[1-[(2,6-dichlorophenyl)methyl]-3-(1-pyrrolidinylmethyl)-1-indol-6-yl]carbonyl]-3,4-difluoro-L-phenylalanyl-N-(2-aminoethyl)-3-(4-pyridinyl)-(Compound 175)

Methyl-3-formylindole-6-carboxylate AE1 (5.00 g, 24.6 mmol) was dissolved in dry DMF (66 mL) under nitrogen and cesium carbonate (8.01 g, 24.6 mmol) was added. The mixture was stirred at rt for 10 min. After stirring for 10 min, 2,6-dichlorobenzyl bromide (5.90 g, 24.6 mmol) was added and the reaction stirred at rt for 20 h. The reaction mixture was filtered and the filtrate was diluted with CH₂Cl₂, washed with equal volumes of H₂O (5×), then dried (MgSO₄) and evaporated in vacuo to a solid. The solid (3.59 g, 9.9 mmol) was dissolved in ClCH₂CH₂Cl:AcOH (100:1) under nitrogen, pyrrolidine (3.30 mL, 39.6 mmol) and NaB(OAc)₃H (5.23 g, 24.7 mmol) were added and the mixture stirred at rt for 1.5 h. The reaction mixture was then diluted with EtOAc (200 mL), washed with H₂O (2×100 mL) and brine (1×100 mL), then dried (NaSO₄) and evaporated in vacuo to a solid. The solid (4.05 g, 9.7 mmol) was suspended in THF (100 mL) under nitrogen, KOSiMe₃ (3.73 g, 29.1 mmol) was added and the reaction was stirred at rt for 72 h. Additional KOSiMe₃ (1.24 g, 9.7 mmol) was added and the reaction was stirred at 40° C. for 6 h. After cooling to rt, the reaction mixture was evaporated in vacuo and dried. The resulting residue was dissolved in H₂O (30 mL), the pH was adjusted to about pH 6 with 6N HCl and the product was extracted with EtOAc, which precipitated a solid. The yellow solid was filtered and dried to afford AE2. The resin AE3 was then agitated in DMF (8 mL) with AE2 (0.097 g, 0.24 mmol), HOBT (0.041 g, 0.30 mmol) and DCC (0.062 g, 0.30 mmol) at rt for 20 h. The solution was drained; the resin was then washed with DMF (3×), MeOH (3×) and CH₂Cl₂ (3×) and dried in vacuo for about 2 h. The resin was combined with TFA:CH₂Cl₂:anisole (30:70:1.0, 8 mL) and stirred at about rt for about 1.5 h. The resin was filtered and the filtrate was blown down with nitrogen overnight to an oil, which was triturated with ether (4×) to give Compound 175 as a tan solid. ¹H NMR (CD₃OD) δ 8.55 (d, J=6.1, 2H), 8.20 (s, 1H), 7.84–7.79 (m, 3H), 7.64–7.38 (m, 5H), 7.25–7.11 (m, 3H), 5,71 (s, 2H), 4.78–4.71 (m, 2H), 4.52 (s, 2H), 3.55–3.01 (m, 12H), 2.11–1.97 (m, 4H). ES-MS m/z 776 (MH⁺).

Example 6

As a specific embodiment of an oral composition, about 100 mg of the Compound 46 of Example 1 is formulated with sufficient finely divided lactose to provide a total amount of about 580 mg to about 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the following formula (I):

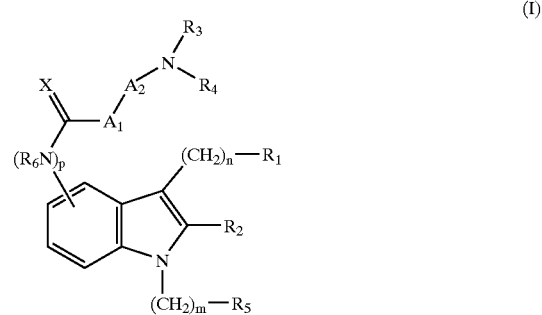

wherein:

$A_1$ and $A_2$ are each independently a D- or L-amino acid selected from the group consisting of alanine, β-alanine, arginine, homoarginine, cyclohexylalanine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3-diaminopropionic acid (optionally substituted with acyl, $C_1$–$C_4$ alkyl, aroyl, amidino, or MeC(NH)—), glutamine, glycine, indanylglycine, lysine (optionally substituted with acyl, $C_1$–$C_4$ alkyl, aroyl, MeC(NH)—), valine, methionine, proline, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), tetrahydroisoquinoline-3-COOH, threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$R_1$ is selected from amino, $C_1$–$C_8$ alkylamino, $C_1$–$C_8$ dialkylamino, arylamino, ar$C_1$–$C_8$ alkylamino, $C_3$–$C_8$ cycloalkylamino, heteroalkyl$C_1$–$C_8$ alkylamino, heteroalkyl$C_1$–$C_8$ alkyl-N-methylamino, $C_1$–$C_8$ dialkylamino$C_1$–$C_8$ alkylamino, —N($C_1$–$C_8$alkyl)-$C_1$–$C_8$ alkyl-N($C_1$–$C_8$ alkyl)$_2$, N($C_1$–$C_8$ alkyl)($C_1$–$C_8$ alkenyl), —N($C_1$–$C_8$alkyl)($C_3$–$C_8$cycloalkyl), heteroalkyl or substituted heteroalkyl wherein the substituent on the heteroalkyl is selected from oxo, amino, $C_1$–$C_8$ alkoxy$C_1$–$C_8$ alkyl, $C_1$–$C_8$ alkylamino or $C_1$–$C_8$ dialkylamino;

$R_2$ is selected from hydrogen, halogen, $C_1$–$C_8$ alkyl, $C_3$–$C_8$ cycloalkyl, $C_1$–$C_8$ alkenyl, $C_1$–$C_8$ alkynyl, ar$C_1$–$C_8$ alkyl, aryl or heteroaryl;

$R_3$ and $R_4$ are each independently selected from hydrogen, $C_1$–$C_8$ alkyl, $C_3$–$C_8$ cycloalkyl, $C_3$–$C_8$ cycloalkyl$C_1$–$C_8$ alkyl, aryl, heteroalkyl, substituted heteroalkyl (wherein the substituent on the heteroalkyl is one or more substituents independently selected from $C_1$–$C_8$ alkoxycarbonyl, $C_1$–$C_8$ alkyl, or $C_1$–$C_4$ alkylcarbonyl), heteroalkyl$C_1$–$C_8$ alkyl, indanyl, acetamidino$C_1$–$C_8$ alkyl, amino$C_1$–$C_8$ alkyl, $C_1$–$C_8$ alkylamino$C_1$–$C_8$ alkyl, $C_1$–$C_8$ dialkylamino$C_1$–$C_8$ alkyl, unsubstituted or substituted heteroaryl$C_1$–$C_8$ alkyl, or unsubstituted or substituted ar$C_1$–$C_8$ alkyl, wherein the substituent on the aralkyl or heteroarylalkyl group is one or more substituents independently selected from halogen, nitro, amino, $C_1$–$C_8$ alkyl, $C_1$–$C_8$ alkoxy, hydroxy, cyano, $C_1$–$C_4$ alkylcarbonyl, $C_1$–$C_8$ alkoxycarbonyl, hydroxy$C_1$–$C_8$ alkyl or aminosulfonyl; or $R_3$ and $R_4$, together with the nitrogen to which they are attached, alternatively form an unsubstituted or substituted heteroalkyl group selected from piperidinyl, piperazinyl, morpholinyl or pyrrolidinyl, wherein the substituent is one or more substituents independently selected from $C_1$–$C_8$ alkyl $C_1$–$C_8$ alkoxycarbonyl or $C_1$–$C_4$ alkylcarbonyl;

$R_5$ is selected from unsubstituted or substituted aryl, ar$C_1$–$C_8$ alkyl, $C_3$–$C_8$ cycloalkyl, or heteroaryl, where the substituents on the aryl, ar$C_1$–$C_8$ alkyl, cycloalkyl or heteroaryl group are independently selected from one or more of halogen, nitro, amino, cyano, hydroxyalkyl, $C_1$–$C_8$ alkyl, $C_1$–$C_8$ alkoxy, hydroxy, $C_1$–$C_4$ alkylcarbonyl, $C_1$–$C_8$ alkoxycarbonyl, fluorinated $C_1$–$C_4$ alkyl, fluorinated $C_1$–$C_4$ alkoxy or $C_1$–$C_4$ alkylsulfonyl;

$R_6$ is selected from hydrogen or $C_1$–$C_8$ alkyl;

X is oxygen or sulfur;

m is an integer selected from 0, 1, 2 or 3;

n is an integer selected from 1 or 2; and p is an integer selected from 0 or 2;

and pharmaceutically acceptable salts thereof.

2. The compound of claim 1, wherein:

$A_1$ and $A_2$ are each independently an L-amino acid selected from the group consisting of alanine, β-alanine, arginine, homoarginine, cyclohexylalanine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3-diaminopropionic acid (optionally substituted with acyl, $C_1$–$C_4$ alkyl, aroyl, amidino, or MeC(NH)—), glutamine, glycine, indanylglycine lysine (optionally substituted with acyl, $C_1$–$C_4$ alkyl, aroyl, MeC(NH)—), valine, methionine, proline, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), tetrahydroisoquinoline-3-COOH, threonine (optionally substituted with $C_1$–$C_4$ alkyl, aryl, or ar$C_1$–$C_4$ alkyl), ornithine (optionally substituted with acyl, $C_1$–C, alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$R_1$ is selected from amino, $C_1$–$C_6$ alkylamino, $C_1$–$C_6$ dialkylamino, arylamino, ar$C_1$–$C_6$ alkylamino, heteroalkyl$C_1$–$C_6$ alkylamino, —N($C_1$–$C_8$ alkyl)-$C_1$–$C_6$ alkyl-N($C_1$–$C_6$ alkyl)$_2$, heteroalkyl or substituted heteroalkyl wherein the substituent on the heteroalkyl is selected from oxo, amino, $C_1$–$C_8$ alkoxy $C_1$–$C_6$ alkyl, $C_1$–$C_6$ alkylamino or $C_1$–$C_6$ dialkylamino;

$R_2$ is selected from hydrogen, halogen or phenyl;

$R_3$ is selected from hydrogen or $C_1$–$C_8$ alkyl;

$R_4$ is selected from $C_1$–$C_8$ alkyl, $C_3$–$C_6$ cycloalkyl, $C_3$–$C_6$ cycloalkyl$C_1$–$C_6$ alkyl, aryl, heteroaryl$C_1$—$C_6$ alkyl, substituted heteroaryl$C_1$–$C_6$ alkyl wherein the substituent is $C_1$–$C_4$ alkyl, heteroalkyl, heteroalkyl$C_1$–$C_6$ alkyl, indanyl, acetamidino$C_1C_6$ alkyl, amino$C_1$–$C_6$ alkyl, $C_1$–$C_6$ alkylamino$C_1$–$C_6$ alkyl, $C_1$–$C_8$ dialkylamino$C_1$–$C_6$ alkyl, ar$C_1$–$C_6$ alkyl, substituted ar$C_1$–$C_8$ alkyl wherein the substituent on the aralkyl group is one to five substituents independently selected from halogen, nitro, amino, $C_1$–$C_8$ alkyl, $C_1$–$C_6$ alkoxy, $C_1$–$C_6$ alkoxycarbonyl, hydroxyalkyl or aminosulfonyl; or $R_3$ and $R_4$, together with the nitrogen to which they are attached, alternatively form an unsubstituted or substituted heteroalkyl group selected from piperidinyl, piperazinyl or pyrrolidinyl, wherein the substituent is independently one or two substituents selected from $C_1$–$C_6$ alkyl;

$R_5$ is selected from unsubstituted or substituted aryl, ar$C_1$–$C_6$ alkyl, $C_3$–$C_6$ cycloalkyl or heteroaryl, where the substituents on the aryl, aralkyl, cycloalkyl or heteroaryl group are independently selected from one to three substituents selected from halogen, cyano, $C_1$–$C_4$ alkyl, $C_1$–$C_4$ alkoxy, $C_1$–$C_4$ alkoxycarbonyl, fluorinated $C_1$–$C_4$ alkyl, fluorinated $C_1$–$C_4$ alkoxy or $C_1$–$C_4$ alkylsulfonyl;

$R_6$ is hydrogen; and

X is oxygen; and p is 1;

and pharmaceutically acceptable salts thereof.

3. The compound of claim 2, wherein:

$A_1$ is an L-amino acid selected from the group consisting of alanine, arginine, cyclohexylalanine, glycine, proline, tetrahydroisoquinoline-3COOH, and an unsubstituted or substituted aromatic amino acid selected from the group consisting of phenylalanine, naphthylalanine, homophenylalanine, and O-methyl tyrosine, wherein the substituents on the aromatic amino acid are independently one to five substituents selected from halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$A_2$ is an L-amino acid selected from the group consisting of alanine, β-alanine, arginine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3-diaminopropionic acid (optionally substituted with acyl, $C_1$–$C_4$ alkyl, aroyl, amidino, or MeC(NH)—), glutamine, glycine, lysine (optionally substituted with acyl, $C_1$–$C_4$ alkyl, aroyl, MeC(NH)—), valine, methionine, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, and histidine, wherein the substituents of the aromatic amino acid are independently one to five substituents selected from halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$R_2$ is selected from hydrogen, chlorine or phenyl;

$R_3$ is selected from hydrogen or $C_1$–$C_4$ alkyl; and m and n are both 1;

and pharmaceutically acceptable salts thereof.

4. The compound of claim 3 of the formula:

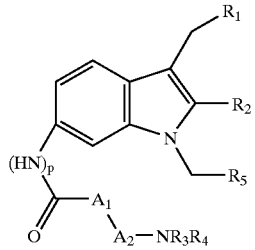

wherein:

$A_1$ is an L-amino acid selected from the group consisting of alanine, arginine, cyclohexylalanine, proline, tetrahydroisoquinoline-3-COOH, and an unsubstituted or substituted aromatic amino acid selected from the group consisting of phenylalanine, naphthylalanine, homophenylalanine, and O-methyl tyrosine, wherein the substituents on the aromatic amino acid are independently one to two substituents selected from halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$A_2$ is an L-amino acid selected from the group consisting of alanine, β-alanine, arginine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3-diaminopropionic acid (optionally substituted with acyl, $C_1$–$C_4$ alkyl, aroyl, amidino, or MeC(NH)—), glutamine, glycine, lysine (optionally substituted with acyl, $C_1$–$C_4$ alkyl, aroyl, MeC(NH)—), valine, methionine, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, and histidine, wherein the substituents on the aromatic amino acid are independently one to two substituents selected from halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$R_1$ is selected from diethylamino, di-(n-propyl)amino,

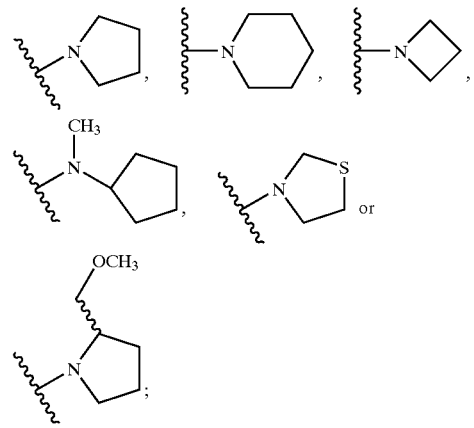

$R_3$ is selected from hydrogen, methyl or ethyl;

$R_4$ is selected from 2-indanyl, phenyl, cyclohexylmethyl, cyclopentyl, pyridylmethyl, furanylmethyl, 2-(4-methyl-furanyl)methyl, thienylmethyl, diphenylmethyl, 4-imidazolylethyl, 2-(4-N-methyl)imidazolylethyl, n-octyl, phenyl-n-propyl, aminoethyl, aminopropyl, amino-n-pentyl, dimethylaminoethyl, 4-aminophenylsulfonylaminomethyl, acetamidineylethyl, 2-N-pyrrolidinylethyl, N-ethoxycarbonylpiperidinyl, unsubstituted or substituted phenylethyl and unsubstituted or substituted benzyl wherein the substituents on the phenylethyl or benzyl are independently one or two substituents selected from methyl, fluorine, chlorine, nitro, methoxy, methoxycarbonyl or hydroxymethyl; or $R_3$ and $R_4$, together with the nitrogen to which they are attached, alternatively form a heteroalkyl group selected from piperidinyl or 4-(N-methyl)piperazinyl; and $R_5$ is selected from cyclohexyl, 2-naphthyl, phenylethyl, 4-fluorophenylethyl, or unsubstituted or substituted phenyl, where the substituents on the phenyl are independently selected from one to two substituents selected from fluorine, chlorine, iodine, methyl, cyano or trifluoromethyl;

and pharmaceutically acceptable salts thereof.

5. The compound of claim 4, wherein:

$R_1$ is 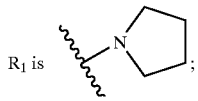;

and pharmaceutically acceptable salts thereof.

6. The compound of claim 5, wherein:
$R_5$ is selected from

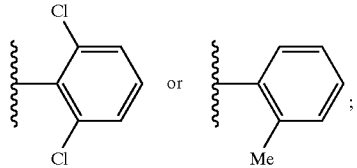

and pharmaceutically acceptable salts thereof.

7. The compound of claim 6, wherein:
$A_1$ is selected from 3,4-Difluorophenylalanine or 4-Chlorophenylalanine;
$A_2$ is selected from 2,4-Diaminobutyric acid or 4-Pyridylalanine;
$R_3$ is hydrogen; and
$R_4$ is selected from benzyl or 2-aminoethyl;
and pharmaceutically acceptable salts thereof.

8. A compound of the formula (II):

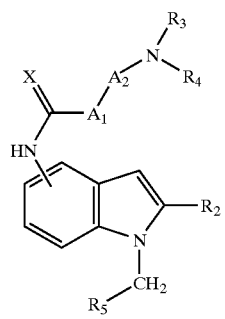

(II)

wherein:
$A_1$ and $A_2$ are each independently a D- or L-amino acid selected from the group consisting of alanine, β-alanine, arginine, homoarginine, cyclohexylalanine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3-diaminopropionic acid (optionally substituted with acyl, $C_1$–$C_4$ alkyl, aroyl, amidino, or MeC(NH)—), glutamine, glycine, indanylglycine, lysine (optionally substituted with acyl, $C_1$–$C_4$ alkyl, aroyl, MeC(NH)—), valine, methionine, proline, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), tetrahydroisoquinoline-3-COOH, threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine, wherein the substituents on the aromatic amino acid are independently selected from one or more of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$R_2$ is selected from hydrogen, halogen, $C_1$–$C_8$ alkyl, $C_3$–$C_8$ cycloalkyl, $C_1$–$C_8$ alkenyl, $C_1$–$C_8$ alkynyl, ar$C_1$–$C_8$ alkyl, aryl or heteroaryl;

$R_3$ and $R_4$ are each independently selected from hydrogen, $C_1$–$C_8$ alkyl, $C_3$–$C_8$ cycloalkyl, $C_3$–$C_8$ cycloalkyl$C_1$–$C_8$ alkyl, aryl, heteroalkyl, substituted heteroalkyl (wherein the substituent on the heteroalkyl is one or more substituents independently selected from $C_1$–$C_8$ alkoxycarbonyl, $C_1$–$C_8$ alkyl, or $C_1$–$C_4$ alkylcarbonyl), heteroalkyl$C_1$–$C_8$ alkyl, indanyl, acetamidino$C_1$–$C_8$ alkyl, amino$C_1$–$C_8$ alkyl, $C_1$–$C_8$ alkylamino$C_1$–$C_8$ alkyl, $C_1$–$C_8$ dialkylamino$C_1$–$C_8$ alkyl, unsubstituted or substituted heteroaryl$C_1$–$C_8$ alkyl, or unsubstituted or substituted ar$C_1$–$C_8$ alkyl, wherein the substituent on the aralkyl or heteroarylalkyl group is one or more substituents independently selected from halogen, nitro, amino, $C_1$–$C_8$ alkyl, $C_1$–$C_8$ alkoxy, hydroxy, cyano, $C_1$–$C_4$ alkylcarbonyl, $C_1$–$C_8$ alkoxycarbonyl, hydroxy$C_1$–$C_8$ alkyl or aminosulfonyl; or $R_3$ and $R_4$, together with the nitrogen to which they are attached, alternatively form an unsubstituted or substituted heteroalkyl group selected from piperidinyl, piperazinyl, morpholinyl or pyrrolidinyl, wherein the substituent is one or more substituents selected from $C_1$–$C_8$ alkyl $C_1$–$C_8$ alkoxycarbonyl or $C_1$–$C_4$ alkylcarbonyl;

$R_5$ is selected from unsubstituted or substituted aryl, ar$C_1$–$C_8$ alkyl, $C_3$–$C_8$ cycloalkyl, or heteroaryl, where the substituents on the aryl, ar$C_1$–$C_8$ alkyl, cycloalkyl or heteroaryl group are independently selected from one or more of halogen, nitro, amino, cyano, hydroxyalkyl, $C_1$–$C_8$ alkyl, $C_1$–$C_8$ alkoxy, hydroxy, $C_1$–$C_4$ alkylcarbonyl, $C_1$–$C_8$ alkoxycarbonyl, fluorinated $C_1$–$C_4$ alkyl, fluorinated $C_1$–$C_4$ alkoxy or $C_1$–$C_4$ alkylsulfonyl; and, X is oxygen or sulfur; and salts thereof.

9. A pharmaceutical composition comprising a pharmaceutically acceptable carrier and a compound of claim 1.

10. A pharmaceutical composition made by mixing a compound of claim 1 and a pharmaceutically acceptable carrier.

* * * * *